US007407940B2

(12) United States Patent
Falla et al.

(10) Patent No.: US 7,407,940 B2
(45) Date of Patent: Aug. 5, 2008

(54) ANTIMICROBIAL HEXAPEPTIDES

(75) Inventors: Timothy J. Falla, Woodinville, WA (US); Lijuan Zhang, Kenmore, WA (US); Scott M. Harris, Seattle, WA (US)

(73) Assignee: Helix BioMedix Inc., Bothell, WA (US)

( * ) Notice: Subject to any disclaimer, the term of this patent is extended or adjusted under 35 U.S.C. 154(b) by 0 days.

(21) Appl. No.: 11/350,192

(22) Filed: Feb. 8, 2006

(65) Prior Publication Data

US 2006/0229252 A1  Oct. 12, 2006

Related U.S. Application Data

(60) Provisional application No. 60/651,270, filed on Feb. 9, 2005.

(51) Int. Cl.
*A61K 38/08* (2006.01)
*C07K 7/06* (2006.01)

(52) U.S. Cl. .......................... 514/17; 530/329
(58) Field of Classification Search ................. None
See application file for complete search history.

(56) References Cited

U.S. PATENT DOCUMENTS

| | | | |
|---|---|---|---|
| 4,355,104 | A | 10/1982 | Hultmark et al. |
| 4,520,016 | A | 5/1985 | Hultmark et al. |
| 5,561,107 | A | 10/1996 | Jaynes et al. |
| 5,620,954 | A | 4/1997 | Maloy |
| 5,717,064 | A | 2/1998 | Julian et al. |
| 5,744,445 | A | 4/1998 | Jaynes et al. |
| 5,789,542 | A | 8/1998 | McLaughlin |
| 5,861,478 | A | 1/1999 | Jaynes |
| 5,962,410 | A | 10/1999 | Jaynes et al. |
| 6,001,805 | A | 12/1999 | Jaynes et al. |
| 6,084,156 | A | 7/2000 | Garbabino |
| 6,191,110 | B1 | 2/2001 | Jaynes et al. |
| 6,255,282 | B1 | 7/2001 | Jaynes |
| 6,303,568 | B1 | 10/2001 | Jaynes et al. |
| 6,331,440 | B1 | 12/2001 | Nordstedt et al. |
| 6,440,935 | B1 | 8/2002 | Jaynes et al. |
| 6,559,281 | B1 | 5/2003 | Jaynes |
| 6,566,334 | B1 | 5/2003 | McLaughlin |
| 6,635,740 | B1 | 10/2003 | Enright et al. |
| 2002/0077298 | A1* | 6/2002 | Little et al. .................... 514/16 |
| 2005/0107289 | A1* | 5/2005 | Ghadiri et al. .................. 514/9 |

FOREIGN PATENT DOCUMENTS

| | | |
|---|---|---|
| EP | 1004595 A | 5/2000 |
| WO | WO 95/19370 | 7/1995 |
| WO | WO 96/03519 A | 2/1996 |
| WO | WO 01/49834 | 7/2001 |
| WO | WO 01/98364 | 12/2001 |

OTHER PUBLICATIONS

U.S. Appl. No. 10/109,171, filed Mar. 28, 2002, Owen.
U.S. Appl. No. 11/136,186, filed May 24, 2005, Owen.

Baghian et al., "An Amphipathic α-Helical Synthetic Peptide Analogue of Melittin Inhibits Herpes Simples Virus-1 (HSV-1)-Induced Cell Fusion and Virus Spread," *Peptides*, 18(2):177-183 (1997).

Bessalle et al., "Structure-Function Studies of Amphiphilic Antibacterial Peptides," J. Med. Chem., 1993, 36:1203-1209.

Blondelle et al., "Lipid-Induced Conformation and Lipid-Binding Properties of Cytolytic and Antimicrobial Peptides: Determination and Biological Specificity," *Biochemica et Biophysica Acta*, 1462:89-108 (1999).

Dathe et al, "Structural Features of Helical Antimicrobial Peptides: Their Potential to Modulate Activity on Model Membranes and Biological Cells," *Biochimica et Biophysica Acta* 1462:71-87 (1999).

De Lucca et al., "Fungicidal Properties, Sterol Binding, and Proteolytic Resistance of the Synthetic Peptide D4E1," *Can. J. Microbiol*, 44:514-520 (1998).

Dushay et al., "Two *attacin* Antibacterial Genes of *Drosophila melanogaster*," *Gene*, 246:49-57 (2000).

Ekengren et al., Drosophila Cecropin as an Antifungal Agent, *Insect Biochemistry and Molecular Biology*, 29:965-972 (1999).

Epand et al., "Diversity of Antimicrobial Peptides and Their Mechanisms of Action," *Biochimica et Biophysica Acta* 1462:11-28 (1999).

Friedrich et al., "Salt-Resistant Alpha-Helical Cationic Antimicrobial Peptides," *Antimicrobial Agents and Chemotherapy*, pp. 1542-1548 (1999).

Giacometti et al., "Antimicrobial Activity of Polycationic Peptides," *Peptide*, 20:1265-1273 (1999).

Giacometti et al., "In-Vitro Activity of Cationic Peptides Alone and in Combination with Clinically Used Antimicrobial Agents Against *Pseudomonas Aeruginosa*," *Journal of Antimicrobial Chemotherapy*, 44:641-645 (1999).

Goraya et al., "Peptides with Antimicrobial Activity from Four Different Families Isolated from the Skins of the North American Frogs *Rana luteiventris, Rana berlandieri* and *Rana pipiens*," *Eur. J. Biochem*, 267:894-900 (2000).

(Continued)

*Primary Examiner*—Jeffrey E Russel
(74) *Attorney, Agent, or Firm*—Howrey LLP

(57) ABSTRACT

The invention encompasses hexapeptides consisting of alternating hydrophobic residues (B) at positions 2, 4, and 6, hydrophilic, charged residues (X) at positions 1 and 3, and a naphthylalanine (Nal), an aliphatic or aromatic residue (O) at position five, represented generally by the formula XBX-BOB, which exhibit antimicrobial activity against infections caused by a variety of pathogens. These pathogens may include gram positive or negative bacteria, acid-fast bacteria such as mycobacteria, parasites, dermatophytes, or fungal pathogens. Typical fungal pathogens include *Candida albicans* and typical dermatophytes include *Trichophyton rubrum* and *Trichophyton mentagrophytes*. The hexapeptides of the present invention exhibit antifungal activity, antibacterial activity, desirable stability, and lack toxicity to the mammal receiving treatment.

26 Claims, 11 Drawing Sheets

OTHER PUBLICATIONS

Hancock et al., "Cationic Peptides: A New Source of Antibiotics," *Tibtech*, 16:82-88 (1998).

Hancock et al., "Peptide Antibiotics," *Antimicrobial Agents and Chemotherapy*, pp. 1317-1323 (1999).

Hancock, "Host Defence (Cationic) Peptides. What is Their Future Clinical Potential?", *Drugs* 4:469-473 (1999).

Hancock, "Peptide Antibiotics," *Lancet*, 349:418-422 (1997).

Hong et al., Structure and Organization of Hemolytic and Nonhemolytic Diastereomers of Antimicrobiol Peptides in Membranes, *Biochemistry*, 38:16963-16973 (1999).

Hung et al., "Membrane Lysis by the Antibacterial Peptides on Cecropins B1 and B3: A Spin-Label Electron Spin Resonance Study on Phospholipid Bilayers," *Biophysical Journal*, 77:3120-3233 (1999).

Jia et al., "Antimicrobial Peptides Protect Coho Salmon from *Vibrio anguillarum* Infections," *Applied and Enviromental Microbiology*, 66(5):1928-1932 (2000).

Juvvadi et al., "Structure-Activity Studies of Normal and Retro Pig Cecropin-Melittin Hybrids," *J. Peptide Res.*, 53:244-251 (1999).

Katayama, Kou et al., "A Pentapeptide from Type I Procollagen Promotes Extracellular Matrix Production," *The Journal of Biological Chemistry*, 268(14):9941-9944 (1993.

Kondejewski et al, "Dissociation of Antimicrobial and Hemolytic Activities in the Cyclic Peptide Diastereomers by Systematic Alterations in Amphipathicity," *The Journal of Biological Chemistry*, 274(19):13181-13192 (1999).

Lowenberger et al., Antimicrobial Activity Spectrum, cDNA Cloning, and mRNA Expression of a Newly Isolated Member of the Cecropin Family from the Mosquito Vector *Aedes aegypti*, *The Journal of Biological Chemistry*, 274(29):20092-20097 (1999).

Martin et al., "Evaluation of the Effect of Peptidyl Membrane-Interactive Molecules on Avian Coccidia," *Parasitol Res.*, 85:331-336 (1999).

McInnes et al., "Development of the Structural Basis for Antimicrobial and Hemolytic Activities of Peptides Based on Gramicidin S and Design of Novel Analogs Using NMR Spectroscopy," *The Journal of Biological Chemistry*, 275(19):14287-14294 (2000).

Oh et al., "Activities of Synthetic Hybrid Peptides Against Anaerobic Bacteria: Aspects of Methodology and Stability," *Antimicrobial Agents and Chemotherapy*, pp. 68-72 (2000).

Oh et al., "Cationic Peptide Antimicrobials Induce Selective Transcription of *micF* and *osmY* in *Escherichia coli*," *Biochimica et Biophysica Acta*, 1463:43-54 (2000).

Oh, J.E., et al., "Design, Synthesis and Characterization—(A Model Decapeptide)," J. Peptide Res., 1999, 54:129-136.

Osapay et la., "Formation and Characterization of a Single Trp-Trp Cross-Link in Indolicidin that Confers Protease Stabilty Without Altering Antimicrobial Activity," *The Journal of Biological Chemistry*, 275(16):12017-12022 (2000).

Reed et al., Interleukin 2 Promoter/Enhancer Controlled Expression of a Synthetic Cecropin-Class Lytic Peptide in Transgenic Mice and Subsequent Resistance to *Brucella abortus*, *Transgenic Research*, 6:337-347 (1997).

Robertson et al., "Peptidyl Membrane-Interactive Molecules are Cytotoxic to Prostatic Cancer Cells in vitro," *World J. Urol.*, 16:405-409 (1998).

Rocca et al., "Simulation Studies of the Interaction of Antimicrobial Peptides and Lipid Bilayers," *Biochemica et Biophysica Acta*, 1462:185-200 (1999).

Schwab et al., "In Vitro Activities of Designated Antimicrobial Peptides Against Multidrug-Resistant Cystic Fibrosis Pathogens," *Antimicrobial Agents and Chemotherapy*, pp. 1435-1440 (1999).

Scott et al., "Biological Properties of Structurally Related α-Helical Cationic Antimicrobial Peptides," *Infection and Immunity*, 67(4):2005-2009 (1999).

Scott et al., "Cutting Edge: Cationic Antimicrobial Peptides Block the Binding of Lipopolysaccharide (LPS) to LPS Binding Protein," *The Journal of Immunology*, pp. 549-533 (2000).

Shin et al., "Effects of the Hinge Region of Cecropin A(1-8)-Magainin 2(1-12), a Synthetic Antimicrobial Peptide, on Liposomes; Barterial and Tumor Cells," *Biochemica et Biophysica Acta*, 1463:209-218 (2000).

Shin et al., "Strucure-Antibacterial, Antitumor and Hemolytic Activity Relationship of Cecropin A-magainin 2 and Cecropin A-Melittin Hybrid Peptides," *J. Peptide Res.*, 53:82-90 (1999).

Silvestro, et al. "Antibacterial and Antimembrane Activities of Cecropin A in *Escherichia coli*", *Antimicrobial Agents and Chemotherapy*, pp. 602-607 (2000).

Wang et al, "The Effect of pH on the Structure, Binding and Model Membrane Lysis by Cecropin B and Analogs," *Biochimica et Biophysica Acta* 1473:418-430 (1999).

Wu et al., "Improved Derivatives of Bactenecin, a Cyclic Dodecameric Antimicrobial Cationic Peptide," *Antimicrobial Agents and Chemotherapy*, pp. 1274-1276 (1999).

Wu et al., Mechanism of Interaction of Different Classes of Cationic Antimicrobial Peptides with Planar Bilayers and with the Cytoplasmic Membrane of *Escherichia coli*, 38:7235-7242 (1999).

Zboinska et al., Antibacterial activity of phosphono dipeptides based on 1-amino-1-methylethanephosphonic acid. FEMS Microbiology Letters. 1990, vol. 70, pp. 23-28, especially pp. 23 and 25-27.

Zhang et al, "Determinants of Recombinant Production of Antimicrobial Cationic Peptides and Creation of Peptide Variants in Bacteria," *Biochemical and Biophysical Research Communications*, 274:674-680 (1998).

Zhang et al., "Influence of Proline Residues on the Antibacterial and Synergistic Activities of α-Helical Peptides," *Biochemistry*, 38:8102-8111 (1999).

Supplementary European Search Report for EP 02 72 5386 dated Jul. 28, 2005.

Form PCT/ISA/220 International Search Report dated Oct. 3, 2002.

PCT Written Opinion dated Dec. 13, 2002; pp. 1-5.

Response to Written Opinion filed Feb. 12, 2003; pp. 1-15.

PCT Notification of Transmittal of International Preliminary Examination Report dated Apr. 30, 2003; pp. 1-17.

Lopez-Garcia Belen et al., "Identification Of Novel Hexapeptides Bioactive Against Phytophathogenic Fungi Through Screening Of A Synthetic Peptide Combinatorial Library," Applied and Enviromental Microbiology, vol. 68, No. 5, (May 2002), pp. 2453-2460.

Strom Morten B et al., "Antimicrobial Activity Of Short Arginine And Tryptohplan-Rich Peptides," Journal of Peptide Science, vol. 8 (Aug. 2002), pp. 431-437.

Strom Morten B et al., "The Pharmacophore Of Short Cationic Antibacterial Peptides," Journal of Medicinal Chemistry, vol. 46, No. 9 (Apr. 24, 2003), pp. 1567-1570.

Wessolowski A et al., "Antimicrobial Activity Of Arginine—And Tryptophan-Rich Hexapeptieds: The Effects Of Aromatic Clusters, D-Amino Acid Substitution And Cyclization," The Journal of Peptide Research, vol. 64, No. 4 (Oct. 2004), pp. 159-169.

* cited by examiner

ANTIMICROBIAL HEXAPEPTIDES

PRIORITY CLAIM

This application claims priority to U.S. provisional application 60/651,270 filed Feb. 9, 2005 and incorporates by reference herein the entire contents thereof.

FIELD OF THE INVENTION

The invention relates to compositions and methods comprising antimicrobial hexapeptides exhibiting desirable biological properties. More specifically, the hexapeptides exhibit desired antifungal and optionally, antibacterial activities. In particular, hexapeptides having charged (hydrophilic) residues at positions one and three; hydrophobic residues at positions two, four, and six; and a naphthylalanine, an aliphatic (such as proline) or an aromatic (such a phenylalanine) residue at position five; represented generally by the formula XBXBOB, are disclosed. Activity can be further enhanced, particularly in serum, by the addition of a lipid moiety to the N-terminus of certain of these peptides. Additionally, amidation at the C-terminus appears to increase activity.

DESCRIPTION OF RELATED ART

Researchers have been developing antimicrobial treatments and agents for decades. Recently, there has been a need for new antimicrobial agents for treating an increasing number of drug-resistant bacterial, viral, and fungal infections.

Various bioactive peptides have been reported in both the scientific literature and in issued patents. Peptides historically have been isolated from natural sources, and have recently been the subject of structure-function relationship studies. Additionally, natural peptides have served as starting points for the design of synthetic peptide analogs.

A review of peptide antibiotics was published by R. E. W. Hancock in 1997 (*Lancet* 349: 418-422). The structure, function, and clinical applications of various classes of peptides were discussed. An additional review of cationic peptide antibiotics was published in 1998 (Hancock, R. E. W. and Lehrer, R. *Trends Biotechnol.* 16: 82-88). The peptides are typically cationic amphipathic molecules of 12 to 45 amino acids in length. The peptides permeabilize cell membranes leading to the control of microbial agents. The clinical potential of host defense cationic peptides was discussed by R. E. W. Hancock in 1999 (*Drugs* 57(4): 469-473; *Antimicrobial Agents and Chemotherapy* 43(6): 1317-1323). The antibacterial, antifungal, antiviral, anticancer, and wound healing properties of the class of peptides are discussed.

Reviews of the structural features of helical antimicrobial peptides, and their presumed mechanisms of action have also been published (see, for example, Dathe, M. and Wieprecht, T. *Biochimica et Biophysica Acta* 1462: 71-87 (1999); Epand, R. M. and Vogel H. J. *Biochimica et Biophysica Acta* 1462: 11-28 (1999)). Structural parameters believed to be capable of modulating activity and selectivity include helicity, hydrophobic moment, hydrophobicity, angle subtended by the hydrophilic/hydrophobic helix surfaces, and charge.

A wide array of naturally occurring alpha helical peptides have been reported. Several representatives of the many references in the field are described herein. Cecropins are a family of α-helical peptides isolated from insects. Cecropins are known for their antibacterial properties, as described in U.S. Pat. Nos. 4,355,104 and 4,520,016. The cecropins were generally found to have activity against certain gram-negative bacteria. Cecropins were found to have no activity against eukaryotic cells (Andreu, et al., *Biochemistry* 24: 163-188 (1985); Boman, et al., *Developmental and Comparative Immunol.* 9: 551-558 (1985); Steiner et al., *Nature* 292: 246-248 (1981)). Cecropins from *Drosophila* and *Hyalphora* were presented as having activity against various strains of fungi (Ekengren, S. and Hultmark, D., *Insect Biochem. and Molec. Biol.* 29: 965-972 (1999)). Cecropin A from mosquito *Aedes aegypti* is reportedly different from most insect cecropins in that it lacks tryptophan and C-terminal amidation (Lowenberger, C. et al., *J. Biol. Chem.* 274(29): 20092-20097 (1999)).

Frogs from the genus *Rana* produce a wide array of antimicrobial peptides in their skin (Goraya, J. et al., *Eur. J. Biochem.* 267: 894-900 (2000)). Peptides as short as 13 amino acids were reported, and were grouped into structural families. The sequences showed little or no sequence identity to peptides isolated from frogs of other genera, such as the magainin and dermaseptin peptides. Magainin is an α-helical 23 amino acid peptide isolated from the skin of the African frog *Xenopus laevis* (Zasloff, M. *Proc. Natl. Acad. Sci. U.S.A.* 84: 5449-5453 (1987).

U.S. Pat. No. 5,962,410 discloses the inhibition of eukaryotic pathogens, and the stimulation of lymphocytes and fibroblasts with lytic peptides such as cecropins and sarcotoxins. Various peptides presented include Cecropin B, Cecropin SB-37, Cecropin A, Cecropin D, Shiva-1, Lepidopteran, Sarcotoxin 1A, Sarcotoxin 1B, and Sarcotoxin 1C.

Transgenic mice producing the Shiva-1 cecropin class lytic peptide were reported by Reed, W. A. et al., *Transgenic Res.* 6: 337-347 (1997). Infection of the transgenic mice with a *Brucella abortus* challenge resulted in a reduction of the number of bacteria relative to infection of non-transgenic mice.

Cathelin associated α-helical peptides of 23 to 38 amino acids are found in the blood cells of sheep, humans, cattle, pigs, mice, and rabbits (Zanetti, M. et al., *FEBS Lett.* 374: 1-5 (1995)).

The antimicrobial activities of buforin II, cecropin P1, indolicidin, magainin II, nisin, and ranalexin were reported by Giacomette, A. et al. (*Peptides* 20: 1265-1273 (1999)). The peptides showed variable activities against bacteria and yeast.

Various synthetic peptides have been prepared and assayed both in vitro and in vivo. For example, U.S. Pat. No. 5,861,478 disclosed synthetic lytic peptides of about 20 to 40 amino acids that adopt an α-helical conformation. The peptides are effective in the treatment of microbial infections, wounds, and cancer. The peptides disclosed include cecropin B, SB-37*, LSB-37, SB-37, Shiva 1 and 10-12, β-fibrin signal peptide, Manitou 1-2, Hecate 1-3, Anubis 1-5 and 8, and Vishnu 1-3 and 8.

Hecate was described as a synthetic peptide analog of melittin by Baghian, A. et al. (*Peptides* 18(2): 177-183 (1997)). The peptides differ in their charge distribution, but not in their amphipathic alpha helical conformation. Hecate inhibited herpes simplex virus (HSV-1) while not adversely affecting cell growth and protein synthesis.

Synthetic peptides D2A21, D4E1, D2A22, D5C, D5C1, D4E, and D4B were described in Schwab, U. et al., *Antimicrob. Agents and Chemotherapy* 43(6): 1435-1440 (1999). Activities against various bacterial strains were described.

Hybrid peptides made of cecropin and melittin peptides were prepared and assayed by Juvvadi, P. et al. (*J. Peptide Res.* 53: 244-251 (1999)). Hybrids were synthesized to investigate the effects of sequence, amide bond direction (helix dipole), charge, amphipathicity, and hydrophobicity on channel forming ability and on antibacterial activity. Sequence and amide bond direction were suggested to be important structural requirements for the activity of the hybrids.

A 26 amino acid insect cecropin—bee melittin hybrid, and analogs thereof, were described in a study of salt resistance (Friedrich, C. et al., *Antimicrobial Agents and Chemotherapy* 43(7): 1542-1548 (1999)). A tryptophan residue in the second position was found to be critical for activity. Modest changes in sequence were found to lead to substantial changes in the properties of the peptides.

The effects of proline residues on the antibacterial properties of α-helical peptides have been published (Zhang, L. et al., *Biochem.* 38: 8102-8111 (1999)). The addition of prolines was reported to change the membrane insertion properties, and the replacement of a single proline may change an antimicrobial peptide into a lytic toxin.

A series of peptides having between 18 and 30 amino acids were prepared in order to test the effects of changes in sequence and charge on antibacterial properties (Scott, M. G., et al., *Infect. Immun.* 67(4): 2005-2009 (1999)). No significant correlation was found between length, charge, or hydrophobicity and the antimicrobial activity of the peptides. A general trend was found that shorter peptides were less active than longer peptides, although it was noted that this effect would probably be sequence dependent.

"Modellins", a group of synthetic peptides were prepared and assayed to compare sequence and structure relationships (Bessalle, R. et al. *J. Med. Chem.* 36: 1203-1209 (1993)). Peptides of 16 and 17 amino acids having hydrophobic and hydrophilic opposite faces were highly hemolytic and antibacterial. Smaller peptides tended to have lower biological activities.

A cecropin-melittin hybrid peptide and an amidated flounder peptide were found to protect salmon from *Vibrio anguillarum* infections in vivo (Jia, X. et al., *Appl. Environ. Microbiol.* 66(5): 1928-1932 (2000)). Osmotic pumps were used to deliver a continuous dose of either peptide to the fish.

Amphipathic peptides have been reported as being capable of enhancing wound healing and stimulating fibroblast and keratinocyte growth in vivo (U.S. Pat. Nos. 6,001,805 and 5,561,107). Transgenic plants have been reportedly prepared expressing lytic peptides as a fusion protein with ubiquitin (U.S. Pat. No. 6,084,156). Methylated lysine rich lytic peptides were reportedly prepared, displaying improved proteolytic resistance (U.S. Pat. No. 5,717,064).

Assignee Helix BioMedix, Inc. is the owner of several additional issued patents and patent publications teaching lytic peptides and methods for their use. U.S. Pat. No. 6,440,935 describes the stimulative and proliferative uses of peptides having about 30 to about 40 amino acids arranged at least in part in an alpha-helical conformation. U.S. Pat. No. 6,303,568 describes methods of treating animals infected with a fungus or gram negative bacteria. The treatment involves administration of a peptide such as Cecropin C-37. U.S. Pat. No. 6,255,282 describes methods of killing microbes involving the administration of various peptides. The peptides are defined by their conformational and sequence properties. Published U.S. Patent Application No. 20020025918 describes the use of similar peptides in plants. Published U.S. Patent Application Nos. 20030109452 and 20030083243 describe short bioactive "FLAK" peptides and methods for their use.

Various patents exist describing cosmetic compositions containing short peptides. For example, U.S. Pat. No. 6,492,326 suggests the preparation and use of skin care compositions containing pentapeptides and skin care active ingredients.

Strom et al. 2003 (Journal of Medicinal Chemistry 46: 1567-1570) describe short antibacterial peptides focused mainly on very short peptides (dimmers and trimers) containing chemical modifications. Certain hexapeptides are also described. However, there is no testing or discussion of antimicrobial or specifically, any anti-fungal activity of these hexapeptides.

Lopez Garcia et al. (*Int. Journal of Food Microbiol.* 89: 163-170 (2003) and *Applied and Environ. Microbiol.* 68: 2453-2460, (2002)) described the screening of a synthetic peptide combinatorial library that resulted in the identification of antifungal hexapeptides with activity against the phytopathogenic fungi crop pathogens. These antifungal peptides contained the motif of RKT or RKK as the first three residues. No testing or discussion of antimicrobial activity against clinically significant pathogens, including fungal pathogens is described. Similarly, there is no discussion of the hexapeptides' stability or toxicity properties.

Thus, there is a need to develop peptides having a broad range of potent antimicrobial activity against a number of microorganisms, including gram negative and gram positive bacteria, protozoa, viruses and the like, and especially against eukaryotic pathogens such as fungi. Since fungal pathogens are eukaryotic, and therefore relatively more similar to the human host than to prokaryotic bacteria, it has traditionally been more difficult to develop effective therapies against eukaryotic pathogens that lack toxicity. This is also the case with developing antifungal peptides.

In addition, antifungal peptides have tended to be relatively long (>15 amino acids) and therefore associated with toxicity, and also exhibit high susceptibility to proteases, low tissue penetration and high cost. Additionally, antimicrobial peptides although good drug candidates for topical applications, are traditionally not compatible with the systemic circulation that would accompany systemic administration.

SUMMARY OF THE INVENTION

The present invention provides antimicrobial hexapeptides comprising hydrophilic, charged residues (X), at positions one and three; hydrophobic residues (B) at positions two, four, and six; and a naphthylalanine, an aliphatic or an aromatic residue (O) at position five; wherein the hexapeptide structure is represented by the formula XBXBOB.

In certain embodiments, the hexapeptide will comprise the following amino acids, wherein X is selected from the group consisting of Arginine (R) and Lysine (K); B is selected from the group consisting of Phenylalanine (F) and Tryptophan (W); and O is selected from the group consisting of naphthylalanine (Nal), Proline (P), and Phenylalanine (F).

In other embodiments, the hexapeptide may be selected from the group consisting of wherein the hexapeptide is selected from the group consisting of KFKWPW-NH$_2$ (SEQ ID NO:1), KWRWPW-NH$_2$ (SEQ ID NO:2), KWKWFW-NH$_2$ (SEQ ID NO:3), RWRWPW-NH$_2$ (SEQ ID NO:4), KFKWFW-NH$_2$ (SEQ ID NO:6), RFKWFW-NH$_2$ (SEQ ID NO:7), OCT-KFKWPW-NH$_2$ (SEQ ID NO:55), OCT-KWK-WFW-NH$_2$ (SEQ ID NO:56), KWKWUW-NH$_2$ (SEQ ID NO:62), and KWKWZW-NH$_2$ (SEQ ID NO:63).

In certain embodiments the hexapeptide is SEQ ID NO:1.

In other embodiments, the hexapeptide is modified. These modifications may include lipidation or amidation.

In other embodiments, the hexapeptide is lipidated and the lipid is selected from the group consisting of heptanoic acid, nonanoic acid, lauric acid, myristic acid, pentadecanoic acid, undecanoic acid, tridecanoic acid, or octanoic acid.

In yet other embodiments, the hexapeptide is selected from the group consisting of Hep- KFKWPW-NH₂ (SEQ ID NO:69), Non- KFKWPW-NH₂ (SEQ ID NO:70), Lau- KFK-WPW-NH₂ (SEQ ID NO:72), Myr- KFKWPW-NH₂ (SEQ ID NO:77), Pen- KFKWPW-NH₂ (SEQ ID NO:78), Und- KFK-WPW-NH₂ (SEQ ID NO:79), Tri- KFKWPW-NH₂ (SEQ ID NO:80), Oct-kfkwpw-NH₂ (SEQ ID NO:81), Lau-kfkwpw-NH₂ (SEQ ID NO:83), and Oct-KFKWPw-NH₂ (SEQ ID NO:84).

In yet other embodiments the hexapeptide is soluble in an aqueous solution.

In certain embodiments the hexapeptide is present in a composition along with a pharmaceutically acceptable carrier. In certain embodiments, the hexapeptide is present in the compositions in a therapeutically effective concentration. This therapeutically effective concentration may be in a range of about 0.0002% to about 90%. In other embodiments, the therapeutically effective concentration is in the range of about 0.5% to about 10%.

In certain embodiments the composition further includes a subcutaneous delivery system. In other embodiments the delivery system may be a topical delivery system. The topical delivery system may be in any form that is selected from the group consisting of a cosmetic preparation, powder, emulsion, lotion, spray, ointment, aerosol, cream, and foam.

In another embodiment, a therapeutically effective amount of the hexapeptide is used for treating or preventing a fungal or bacterial infection in a mammal.

The invention provides compositions useful for treating mammalian tissue, the compositions will generally comprise a hexapeptide that comprises charged residues at positions one and three; hydrophobic residues at positions two, four, and six; and a naphthylalanine, an aliphatic, or an aromatic residue at position five; wherein the hexapeptide structure is represented by the formula XBXBOB.

In yet another embodiment, the invention provides a composition useful for treating microbial infections, said composition being comprised of a hexapeptide selected from the group consisting of KFKWPW-NH₂ (SEQ ID NO:1), KWR-WPW-NH₂ (SEQ ID NO:2), KWKWFW-NH₂ (SEQ ID NO:3), RWRWPW-NH₂ (SEQ ID NO:4), KFKWFW-NH₂ (SEQ ID NO:6), RFKWFW-NH₂ (SEQ ID NO:7), OCT-KFKWPW-NH₂ (SEQ ID NO:55), OCT-KWKWFW-NH₂ (SEQ ID NO:56), KWKWUW-NH₂ (SEQ ID NO:62), KWK-WZW-NH₂ (SEQ ID NO:63), Hep-KFKWPW-NH₂ (SEQ ID NO:69), Non- KFKWPW-NH₂ (SEQ ID NO:70), Lau-KFK-WPW-NH₂ (SEQ ID NO:72), Myr- KFKWPW-NH₂ (SEQ ID NO:77), Pen- KFKWPW-NH₂ (SEQ ID NO:78), Und- KFK-WPW-NH₂ (SEQ ID NO:79), Tri-KFKWPW-NH₂ (SEQ ID NO:80), Oct-kfkwpw-NH₂ (SEQ ID NO:81), Lau-kfkwpw-NH₂ (SEQ ID NO:83), and Oct-KFKWPw-NH₂ (SEQ ID NO:84). This composition may further include a pharmaceutical delivery system.

The present invention also provides methods of treating or preventing microbial infections in mammals, the method being comprised of administering a therapeutically effective concentration of at least one of the hexapeptides of the present invention. In certain embodiments, the hexapeptides are selected from the group consisting of KFKWPW-NH₂ (SEQ ID NO:1), KWRWPW-NH₂ (SEQ ID NO:2), KWKWFW-NH₂ (SEQ ID NO:3), RWRWPW-NH₁ (SEQ ID NO:4), KFKWFW-NH₂ (SEQ ID NO:6), RFKWFW-NH₂ (SEQ ID NO:7), OCT-KFKWPW-NH₂ (SEQ ID NO:55), OCT-KWK-WFW-NH₂ (SEQ ID NO:56), KWKWUW-NH₂ (SEQ ID NO:62), KWKWZW-NH₂ (SEQ ID NO:63), Hep-KFK-WPW-NH₂ (SEQ ID NO:69), Non- KFKWPW-NH₂ (SEQ ID NO:70), Lau- KFKWPW-NH₂ (SEQ ID NO:72), Myr- KFK-WPW-NH₂ (SEQ ID NO:77), Pen- KFKWPW-NH₂ (SEQ ID NO:78), Und- KFKWPW-NH₂ (SEQ ID NO:79), Tri-KFK-WPW-NH₂ (SEQ ID NO:80), Oct-kfkwpw-NH₂ (SEQ ID No:81), Lau-kfkwpw-NH₂ (SEQ ID NO:83), and Oct-KFK-WPw-NH₂ (SEQ ID NO:84).

These methods are useful when the microbial infection is a fungal infection. The methods may also be useful when the microbial infection is a mixed fungal and bacterial infection. The methods may be particularly useful when the fungal infection is caused by a fungus selected from the group consisting of *Candida albicans, Trichophyton rubrum*, and *Trichophyton mentagrophytes*. The methods may also be useful when the bacterial infection is caused by a bacterium selected from the group consisting of *P. aeuroginosa, E. coli*, and *S. aureus*.

In yet another embodiment, the present invention provides a method of inhibiting the growth of a fungal cell comprising contacting said fungal cell with at least one of the hexapeptides of the present invention such that growth of the fungal cell is inhibited. In certain embodiments, the fungal cell is a plant pathogen selected from the group consisting of *Mycosphaerella brassicicola, Pyrenopeziza brassicae, Peronospora destructor*, and *Botrytis squamosa*.

In a further embodiment, the present invention provides a method of preventing microbial infection in mammals, said method being comprised of administering a therapeutically effective concentration of a hexapeptide selected from the group consisting of SEQ ID NO:1, SEQ ID NO:2, SEQ ID NO:3, SEQ ID NO:4, SEQ ID NO:6, SEQ ID NO:7, SEQ ID NO:55, SEQ ID NO:56, SEQ ID NO:62, SEQ ID NO:63, SEQ ID NO:69, SEQ ID NO:70, SEQ ID NO:72, SEQ ID NO:77, SEQ ID NO:78, SEQ ID NO:79, SEQ ID NO:80, SEQ ID NO:81, SEQ ID NO:83, and SEQ ID NO:84.

In yet another embodiment, the present invention provides a pharmaceutical composition comprising a hexapeptide selected from the group consisting of SEQ ID NO:1, SEQ ID NO:2, SEQ ID NO:3, SEQ ID NO:4, SEQ ID NO:6, SEQ ID NO:7, SEQ ID NO:55, SEQ ID NO:56, SEQ ID NO:62, SEQ ID NO:63, SEQ ID NO:69, SEQ ID NO:70, SEQ ID NO:72, SEQ ID NO:77, SEQ ID NO:78, SEQ ID NO:79, SEQ ID NO:80, SEQ ID NO:81, SEQ ID NO:83, and SEQ ID NO:84.

DESCRIPTION OF THE FIGURES

The following figures form part of the present specification and are included to further demonstrate certain aspects of the present invention. The invention may be better understood by reference to one or more of these figures in combination with the detailed description of specific embodiments presented herein.

DESCRIPTION OF THE SEQUENCE LISTINGS

Figure 1:
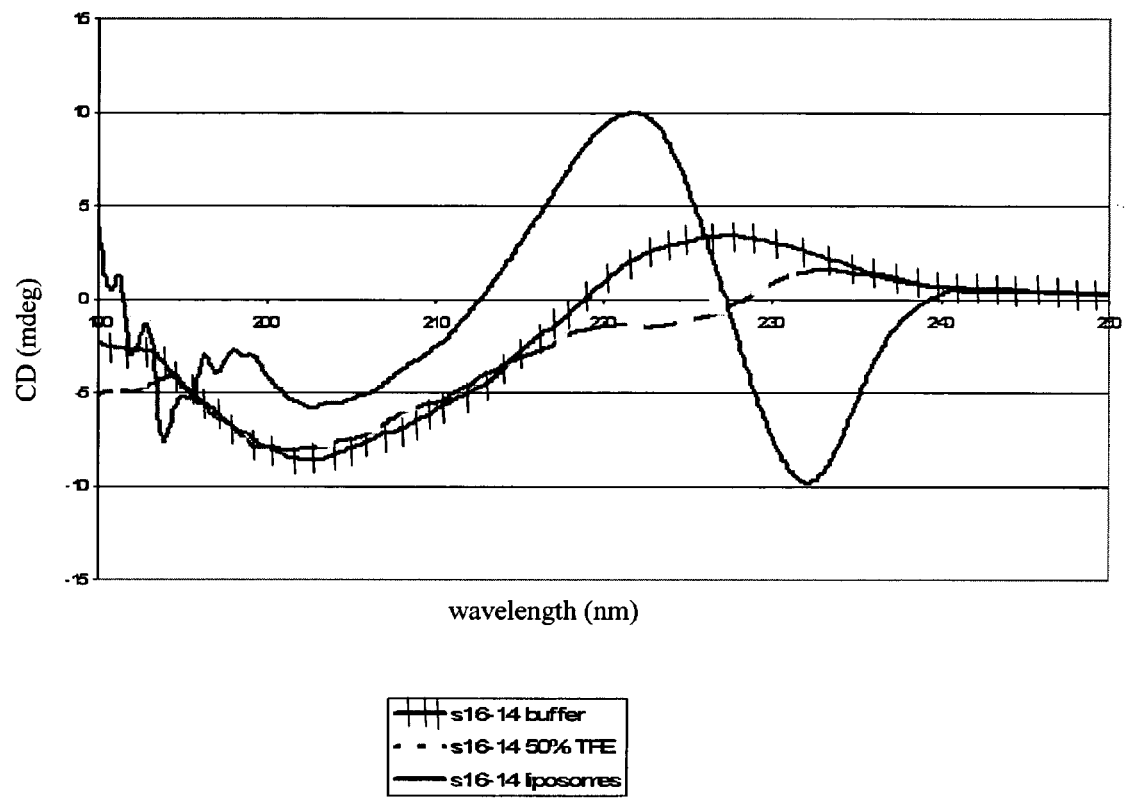
FIG. 1 shows a circular dichroism plot of SEQ ID NO:1 (P0666) demonstrating a shift in structure upon the peptide's interaction with a lipid environment provided in this case by liposomes.

The following amino acid sequence listings form part of the present specification and are included to further demonstrate certain aspects of the present invention. The invention may be better understood by reference to one or more of these sequences in combination with the detailed description of specific embodiments presented herein.

TABLE 1

| SEQ ID NO: | P-No. | Amino Acid Sequence |
|---|---|---|
| 1 | P0666 | KFKWPW-$NH_2$ |
| 2 | P0665 | KWRWPW-$NH_2$ |
| 3 | P0736 | KWKWFW-$NH_2$ |
| 4 | P0735 | RWRWPW-$NH_2$ |
| 5 | P0633 | RWRWRW-$NH_2$ |
| 6 | P0734 | KFKWFW-$NH_2$ |
| 7 | P0737 | RFKWFW-$NH_2$ |
| 8 | P0634 | RRRWWW-$NH_2$ |
| 9 | P0635 | KFKFKF-$NH_2$ |
| 10 | P0636 | KYKYKY-$NH_2$ |
| 11 | P0637 | FKFKFK-$NH_2$ |
| 12 | P0661 | FKFKPV-$NH_2$ |
| 13 | P0662 | VKVKPV-$NH_2$ |
| 14 | P0663 | FALKKL-$NH_2$ |
| 15 | P0664 | RKTWPW-$NH_2$ |
| 16 | P0667 | FKLAPW-$NH_2$ |
| 17 | P0668 | KWKKPV-$NH_2$ |
| 18 | P0669 | FRHFRW-$NH_2$ |

TABLE 1-continued

| SEQ ID NO: | P-No. | Amino Acid Sequence |
|---|---|---|
| 19 | P0670 | VAKLAK-$NH_2$ |
| 20 | P0671 | FAKLAK-$NH_2$ |
| 21 | P0672 | KFKSFK-$NH_2$ |
| 22 | P0673 | KWKKLA-$NH_2$ |
| 23 | P0699 | KWKFKF-$NH_2$ |
| 24 | P0700 | KWKVFK-$NH_2$ |
| 25 | P0701 | VAKKWK-$NH_2$ |
| 26 | P0671 | FAKLAK-$NH_2$ |
| 27 | P0712 | KLAKLL-$NH_2$ |
| 28 | P0713 | LAKLAK-$NH_2$ |
| 29 | P0714 | KPWKFK-$NH_2$ |
| 30 | P0715 | KPVWPW-$NH_2$ |
| 31 | P0716 | KPVKFK-$NH_2$ |
| 32 | P0717 | KFVWPW-$NH_2$ |
| 33 | P0718 | LLKWPW-$NH_2$ |
| 34 | P0719 | FPWKFK-$NH_2$ |
| 35 | P0720 | KPVWPF-$NH_2$ |
| 36 | P0721 | KFFWPF-$NH_2$ |
| 37 | P0738 | KAKFPF-$NH_2$ |
| 38 | P0739 | KFKPFW-$NH_2$ |
| 39 | P1030 | KUKWPW-$NH_2$ |
| 40 | P1013 | KFKLPW-$NH_2$ |
| 41 | P1014 | KFKWPW-COOH |
| 42 | P1016 | KWKWPW-COOH |
| 43 | P1017 | KWKWFW-COOH |
| 44 | P1018 | KFKWFW-COOH |
| 45 | P1020 | FAKWPW-COOH |
| 46 | P1022 | VAKWPW-COOH |
| 47 | P1023 | KWKWPW-$NH_2$ |
| 48 | P1024 | FAKWPW-$NH_2$ |
| 49 | P1025 | VAKWPW-$NH_2$ |
| 50 | P1026 | KWKFPF-$NH_2$ |
| 51 | P1027 | KWKWGW-$NH_2$ |
| 52 | P1028 | KLKWPW-$NH_2$ |
| 53 | P1029 | KWKLAL-$NH_2$ |
| 54 | P1031 | OCT-FALLKL-$NH_2$ |
| 55 | P1032 | OCT-KFKWPW-$NH_2$ |
| 56 | P1033 | OCT-KWKWFW-$NH_2$ |

TABLE 1-continued

| SEQ ID NO: | P-No. | Amino Acid Sequence |
|---|---|---|
| 57 | P1034 | OCT-KFKWFW-NH$_2$ |
| 58 | P1035 | JALLKL-NH$_2$ |
| 59 | P1036 | KJKWPW-NH$_2$ |
| 60 | P1037 | KWKWJW-NH$_2$ |
| 61 | P1038 | KJKWJW-NH$_2$ |
| 62 | P1085 | KWKWUW-NH$_2$ |
| 63 | P1087 | KWKWZW-NH$_2$ |
| 64 | P1007 | KWKWLPW-NH$_2$ |
| 65 | P1008 | KWKWPPW-NH$_2$ |
| 66 | P1109 | KWKWPGW-NH$_2$ |
| 67 | P1011 | KPKWPPW-NH$_2$ |
| 68 | P1012 | KFKWPPW-NH$_2$ |
| 69 | P1145 | Hep-KFKWPW-NH$_2$ |
| 70 | P1146 | Non-KFKWPW-NH$_2$ |
| 71 | P1147 | Cap-KFKWPW-NH$_2$ |
| 72 | P1148 | Lau-KFKWPW-NH$_2$ |
| 73 | P1149 | Pal-KFKWPW-NH$_2$ |
| 74 | P1150 | Ste-KFKWPW-NH$_2$ |
| 75 | P1151 | Ole-KFKWPW-NH$_2$ |
| 76 | P1258 | Aca-KFKWPW-NH$_2$ |
| 77 | P1273 | Myr-KFKWPW-NH$_2$ |
| 78 | P1274 | Pen-KFKWPW-NH$_2$ |
| 79 | P1275 | Und-KFKWPW-NH$_2$ |
| 80 | P1276 | Tri-KFKWPW-NH$_2$ |
| 81 | P1205 | Oct-kfkwpw-HN2 |
| 82 | P1206 | kfkwpw-NH2 |
| 83 | P1343 | Lau-kfkwpw-NH2 |
| 84 | P1304 | Oct-KFKWPw-NH2 |
| 85 | P1345 | Deca-KFKWPW-NH2 |
| 86 | P153 | FALKALKKLKKALKKAL-NH$_2$ |
| 87 | P55 | FAKLLAKALKKLL-NH$_2$ |
| 88 | P50 | VAKKLAKLAKKLAKLAL-NH$_2$ |
| 89 | P43 | FAKLLAKLAKKLL-NH$_2$ |
| 90 | P64 | FAKALKALLKALKAL-NH$_2$ |
| 91 | P650 | FAKALLKALLKALK-NH$_2$ |
| 92 | P146 | KYKKALKKLAKLL-NH$_2$ |

Amino acid feature key: OCT indicates the addition of octanoic acid via an amide bond to the peptide, using standard peptide chemistry. COOH indicates the C-terminus is non-amidated; J is the symbol for a fluoronated phenylalanine; U means 1-Nal-OH and Z means 2-Nal-OH, where Nal is naphthylalanine, an unnatural amino acid being an analog of phenylalanine and alanine. Lipids listed above with abbreviations and coupled similarly to OCT: myr=myristic acid, und=undecanoic acid, pen=pentadecanoic acid, pal=palmitic acid, ste=stearic acid, lau=lauric acid, tri=tridecanoic acid, cap=caproic acid, ole=oleic acid, non=nonanoic acid, hep=heptanoic acid, aca=8-aminocaprylic acid and deca=decanoic acid. Lower case lettering for amino acids indicates D-form residues.

DETAILED DESCRIPTION OF THE INVENTION

In order that the invention herein described may be more fully understood, the following detailed description is set forth. The invention is generally directed towards compositions and methods comprising antimicrobial hexapeptides exhibiting desirable biological properties.

The present invention relates to hexapeptides with antimicrobial activity against a range of antimicrobial pathogens. These pathogens may include gram positive or negative bacteria, acid-fast bacteria such a mycobacteria, parasites, dermatophytes, or fugal pathogens. Typical fungal pathogens include *Candida albicans* and typical dermatophytes include *Trichophyton rubrum* and *Trichophyton mentagrophytes*.

An example of such a hexapeptide is SEQ ID NO:1 (PO666), which has the useful and surprising benefits of lacking systemic toxicity, having reduced susceptibility to protease degradation, having an increased ability to penetrate infected tissue areas (or regions), and being cost effective to manufacture.

The term dermatophytes refers not to a particular fungus but rather is a common shorthand label for a group of three genera of fungi that commonly cause skin diseases in people and animals. These include the genera *Epidermophyton, Trichophyton, and Microsporum*.

Details on techniques for formulation and administration of pharmaceuticals may be found in the latest edition of Remington's Pharmaceutical Sciences (Mack Publishing Co, Easton Pa.). Although local topical delivery is desirable, there are other means of delivery, for example: oral, parenteral, aerosol, intramuscular, subcutaneous, transcutaneous, intramedullary, intrathecal, intraventricular, intravenous, intraperitoneal, or intranasal administration. The present invention can be formulated in a number of carrier vehicles, for example, in a spray; an aerosol; a water and an oil-type emulsion; an oil and water-type emulsion; a face cream or body cream; a sun lotion or after-sun lotion; or other topical administration vehicle.

As used herein, the term "therapeutic" means an agent utilized to treat, combat, ameliorate, prevent or improve an unwanted condition or disease of a patient. The condition being treated in the present invention includes various fungal diseases that commonly affect mammals such as humans, including yeast infections typically caused by *Candida albicans*, and skin infections such as athlete's foot typically caused by *Trichophyton rubrum*, and *Trichophyton mentagrophytes*. Additionally, the hexapeptides of the present invention, and compositions containing them, may provide useful features for inclusion in general skin care and cosmetic formulations, such as various skin cosmetics, skin creams, lotions, sunscreens, and therapeutic lotions or creams such as anti-acne formulations.

I. Peptide Synthesis

All hexapeptides were synthesized using standard Fmoc (9-Fluorenylmethoxycarbonyl) chemistry on an Advanced ChemTech Apex 396 Multiple Peptide Synthesizer. The Apex 396 is equipped with a 40 well reaction block for the production of up to 40 peptides simultaneously at a scale of 0.15 mmol. The peptides can be prepared as either amidated or free acid sequences using standard amino acids. The resin was first washed and pre-swelled with N,N-dimethyl formamide (DMF). The swelling times ranged from 3 minutes to one hour for Rink amide or Wang resins. The Fmoc protecting group was removed with 25% piperidine in DMF for 25 minutes. The resin was then completely washed to remove traces of piperidine. The Fmoc amino acid monomers were pre-activated in an equi-molar solution of HOAt or HOBt in DMF. The solutions were 0.5M concentration. The amide couplings were carried out using HATU PyBop or HBTU as an activation agent and 2.5-5 fold molar excess of amino acid under basic conditions using a hindered base (diisopropylethylamine). The coupling times were 1-1.5 hours followed by a wash and re-coupling to accomplish a double or triple couple before deprotection and continuation of the growing peptide chain. Coupling efficiency was monitored using the standard Kaiser test. Once the peptide synthesis was completed on the resin, the final Fmoc group was removed as above and the sequences were left as the free base. Lipids were attached to the N terminus or side chain amines, as organic acids, using standard peptide chemistry as described above.

Cleavage of the peptide from the acid labile linker was accomplished using 95% trifluoroacetic acid (TFA) and water with the appropriate scavengers added. Cleavage times range from 30 minutes to one hour. The cleaved peptides were immediately removed from the cleavage block and transferred to tubes for the removal of the TFA. The TFA is removed under reduced pressure. The peptides were then ready for purification and analysis via HPLC using a reverse phase C-18 column and Mass Spectrometry. Primary sequence confirmation and preparative purification was accomplished using an LC/MS/MS system (ABI API2000).

The hexapeptides of the invention may be constructed using a variety of amino acid precursors. The peptides may be homogenous compositions containing only D-, L- or cyclic (non-racemic) amino acids. The chemical structure of such amino acids (which term is used herein to include imino acids), regardless of stereoisomeric configuration, may be based upon that of the nineteen or twenty naturally-occurring amino acids: alanine (Ala; A), arginine (Arg; R), asparagine (Asn; N), aspartate (Asp; D), glutamine (Gln; Q), glutamate (Glu; E), glycine (Gly; G), histidine (His; H), isoleucine (Ile; I), leucine (Leu; L), lysine (Lys; K), methionine (Met; M), proline (Pro; P), phenylalanine (Phe; F), serine (Ser; S), threonine (Thr; T), tryptophan (Trp; W), tyrosine (Tyr; Y), and valine (Val; V). Cysteine (Cys; C) is excluded to prevent disulfide linkage problems in the products. The compositions of the invention may also be non-homogenous, containing for instance D-, L- and/or cyclic amino acids. The hexapeptide compositions may also contain amino acids that are other than the naturally-occurring amino acids, such as norleucine, homophenylalanine, ornithine etc. These non-natural amino acids may be selected from compounds that contain amino and carboxylic acid functionality, but may not be alpha amino acids.

Some of the hexapeptides could be modified with various amino acid mimetics or unnatural amino acids, which may provide particularly useful hexapeptides, as they tend to manifest increased stability in vivo. More specifically, non-critical amino acids need not be limited to those naturally occurring in proteins, such as L-.alpha.-amino acids, or their D-isomers, but may include non-natural amino acids as well, such as amino acids mimetics, e.g. D- or L-naphthylalanine; D- or L-phenylglycine; D- or L-2-thieneylalanine; D- or L-1, -2, 3-, or 4-pyreneylalanine; D- or L-3 thieneylalanine; D- or L-(2-pyridinyl)-alanine; D- or L-(3-pyrindinyl)-alanine; D- or L-(2-pyrazinyl)-alanine; D- or L-(4-isopropyl)-phenylglycine; D-(trifluoromethyl)-phenylglycine; D-(trifluoromethyl)-phenylalanine; D-.rho.-fluorophenylalanine; D- or L-.rho.-biphenylphenylalanine; D- or L-.rho.-methoxybiphenylphenylalanine; D- or L-2-indole(alkyl)alanines; and, D- or L-alkylalanines, where the alkyl group can be a substituted or unsubstituted methyl, ethyl, propyl, hexyl, butyl, pentyl, isopropyl, iso-butyl, sec-isotyl, iso-pentyl, or a non-acidic amino acids. Aromatic rings of a nonnatural amino acid include, e.g., thiazolyl, thiophenyl, pyrazolyl, benzimidazolyl, naphthyl, furanyl, pyrrolyl, and pyridyl aromatic rings. Hexapeptide stability can be assayed in a number of ways. For instance, peptidases and various biological media, such as plasma and serum, have been used to test stability. See, e.g., Verhoef, et al., Eur. J. Drug Metab. Pharmacokinetics 11:291 (1986). Half life of the peptides may be conveniently determined using a typical 25% serum (v/v) assay.

It will be recognized, by those of skill in the art, that the hexapeptides of the invention once selected may be modified to contain functionally equivalent amino acid substitutions and yet retain the same or similar antifungal or antibacterial characteristics. The importance of the hydropathic index of amino acids in conferring biological function on a protein has been discussed generally by Kyte and Doolittle (1982). It has been found by these researchers and others that certain amino acids may be substituted for other amino acids having a similar hydropathic index or score and still retain similar if not identical biological activity. As displayed in Table two below, amino acids are assigned a hydropathic index on the basis of their hydrophobicity and charge characteristics. It is believed that the relative hydropathic character of the amino acid determines the secondary structure of the resultant protein, which in turn defines the interaction of the protein with the substrate molecule. Similarly, in peptides whose secondary structure is not a principal aspect of the interaction of the peptide, position within the peptide and the characteristic of the amino acid residue determine the interactions the peptide has in a biological system. It is proposed that biological functional equivalence may typically be maintained where amino acids having no more than a +/−1 to 2 difference in the index value, and more preferably within a +/−1 difference, are exchanged.

TABLE 2

| AMINO ACID | HYDROPATHIC INDEX |
|---|---|
| Isoleucine | 4.5 |
| Valine | 4.2 |
| Leucine | 3.8 |
| Phenylalanine | 2.8 |
| Cysteine/Cystine | 2.5 |
| Methionine | 1.9 |
| Alanine | 1.8 |
| Glycine | −0.4 |
| Threonine | −0.7 |
| Tryptophan | −0.9 |
| Serine | −0.8 |
| Tyrosine | −1.3 |
| Proline | −1.6 |
| Histidine | −3.2 |
| Glutamic Acid | −3.5 |

TABLE 2-continued

| AMINO ACID | HYDROPATHIC INDEX |
|---|---|
| Glutamine | −3.5 |
| Aspartic Acid | −3.5 |
| Asparagine | −3.5 |
| Lysine | −3.9 |
| Arginine | −4.5 |

Thus, for example, isoleucine, which has a hydropathic index of +4.5, can be substituted for valine (+4.2) or leucine (+3.8), and still produce a protein having similar biologic activity. Alternatively, at the other end of the scale, lysine (−3.9) can be substituted for arginine (−4.5), and so on.

Accordingly, these amino acid substitutions are generally based on the relative similarity of R-group substituents, for example, in terms of size, electrophilic character, charge, and the like. In general, although these are not the only such substitutions, the preferred substitutions which take various of the foregoing characteristics into consideration include the following:

TABLE 3

| Original Residue | Exemplary Residue Substitutions |
|---|---|
| Alanine | gly; ser |
| Arginine | lys |
| Asparagine | gln; his |
| Aspartate | glu |
| Cysteine | ser |
| Glutamate | asp |
| Glutamine | asn |
| Glycine | ala |
| Histidine | asn; gln |
| Isoleucine | leu; val |
| Leucine | ile; val |
| Lysine | arg; gln; glu |
| Methionine | met; leu; tyr |
| Serine | thr |
| Threonine | ser |
| Tryptophan | tyr |
| Tyrosine | trp; phe |
| Valine | ile; leu |

A. Stabilizing Peptide Modifications

A variety of modifications can be made to the hexapeptides as long as the desired antimicrobial activity is retained. Some modifications may be used to increase the intrinsic antimicrobial potency of the hexapeptide. Other modifications may facilitate handling of the hexapeptide. Peptide functional groups that may typically be modified include hydroxyl, amino, guanidinium, carboxyl, amide, phenol, imidazol rings or sulfhydryl. Typical reactions of these groups include but are not limited to acetylation of hydroxyl groups by alkyl halides. Carboxyl groups may be esterified, amidated or reduced to alcohols. Carbodiimides or other catalysts may be used to catalyze the amidation of carboxyl groups. The amide groups of asparagine or glutamine may be deamidated under acidic or basic conditions. Acylation, alkylation, arylation or amidation reactions readily occur with amino groups such as the primary amino group of the peptide or the amino group of lysine residues. The phenolic group of tyrosine can be halogenated or nitrated. Examples where solubility of a peptide could be decreased include acylating charged lysine residues or acetylating the carboxyl groups of aspartic and glutamic acids.

Hexapeptides may be conjugated to soluble or insoluble carrier molecules to modify their solubility properties as needed and to increase the local concentrations of hexapeptides in their target areas. The hexapeptide compositions of the invention may also be injected into the vascular system of a plant. Examples of soluble carrier molecules include polymers of polyethyleneglycol and polyvinylpyrrolidone. Examples of insoluble polymers include sand or other silicates or polystyrene, cellulose, or the like. Hexapeptides may also be micro-encapsulated to enhance their stability during seed, soil, or plant application. Plant application may be especially useful for the treatment of various plant fungal diseases. Typical fungal plant pathogens include examples such as the wheat pathogens *Stagonospora nodorum* and *Septoria tritici*, and *hemibiotrophic* pathogens such as the *Colletotrichum* species, and in particular the bean anthracnose pathogen *C. lindemuthianum*. Other common plant fungal pathogens include those such as *Mycosphaerella brassicicola, Pyrenopeziza brassicae, Peronospora destructor,* and *Botrytis squamosa*. Typically, polyester microspheres are used to encapsulate and stabilize the peptides.

B. Large-Scale Peptide Synthesis

Large-scale (up to 60 kg) peptide synthesis in solution or solid-phase will be accomplished once particular peptide compositions are selected to be used en masse. This synthesis requires a careful selection of protecting groups and condensing methods. All starting materials and reagents can be obtained with good purity from chemical suppliers such as Sigma-Aldrich, Inc. Additionally, amino acids can be obtained from suppliers such as Bachem or Novabiochem®. The racemization of amino acid building blocks under coupling conditions can be greatly suppressed or eliminated by the use of new generation reagents, i.e. HOBt, HOAt, HBTU or HATU. Even the solid-phase methodology is presently suitably developed to manufacture pharmaceutical peptides at multiples of at least 10 kg/batch.

C. Large-Scale Synthesis of Peptides in Solution

The solution-phase synthesis allows easy planning with respect to group protection strategy, fragment selection and methods of fragment coupling to minimize racemization. The intermediates can sometimes be isolated simply by crystallization techniques, which may eliminate the need for purification by column chromatography and therefore improve the scale-up potential. The quality of simultaneously-produced fragments can be easily controlled at each step.

D. Large Scale Solid-Phase Synthesis of Peptides

The cost of the more advanced polymers for solid-phase synthesis is usually high. Some of the supports are not available in bulk. However, their properties play an important role in the accessibility of anchored peptide and release of the peptide from the resin in a fully protected, deprotected or modified form. The transition from laboratory to manufacturing scale of solid-phase peptide synthesis (SPPS) is clearly advantageous due to the fact that the entire synthetic process could be easily automated, and the efficiency of the synthetic steps could be monitored and optimized. The production scale activating processes are well known and environmentally harmless. In addition, SPPS allows direct recovery and recycling of excess of amino acid building blocks from the waste filtrates at production scale.

The following references are incorporated specifically by reference herein: Boris Group, "Production of large-scale peptides in solution." Biochem. Soc. Trans., 18(6), 1299-306; Christian Birr, "The transition to solid-phase production of pharmaceutical peptides." Biochem. Soc. Trans., 18(6), 1313-16; and Paul Lloyd-Williams, Fernando Albericio and Ernest Giralt, "Convergent solid-phase peptide synthesis." Tetrahedron 49(48), 11065-11133. Where large-scale syntheses are to be attempted of the peptide compositions of the invention, the methods and materials recited in these references should be followed.

Of course, where it has been determined that an L-amino acid peptide is sufficiently inhibitory (either with or without stabilization), it may be possible to use recombinant DNA expression according to techniques known well to those of skill in the art to produce such peptides in large scale amounts. Where recombinant peptides are produced and where stability of such peptides is desired, the peptide may be protected from attack at each terminus by covalently linking D-amino acids to one or the other or both termini using techniques known to those of skill in the art of peptide chemistry.

E. Microsphere Encapsulation of Peptides

Various methods of microsphere preparation may be used depending upon the hydrophilic or hydrophobic nature of the peptide composition to be encapsulated. Wang, H. T., et al. 1991, "Influence of formulation methods on the in vitro controlled release of protein from poly(ester) microspheres," J. of Controlled Release 17:23-25 is specifically incorporated herein to the extent that it provides methods and materials not addressed herein.

(1) o/o Emulsion method. A TTA-60 titration assembly (Radiometer, Copenhagen, Denmark) will be used in this method for efficient stirring. Poly(DL-lactide/glycolide, 50:50, Dupont) (0.5 g) will be dissolved in methylene chloride (3.3 ml). Spray-dried peptides (25 mg) may then be dispersed in this solution by applying sonification for 30 s in an ultrasonic cleaner (Branson 3200, Branson Cleaning Company, Shelton, Conn.). This suspension may then be passed dropwise through a syringe with a 220 gauge needle into a well-stirred emulsion containing silicone oil (20-30 ml), $CH_2Cl_2$ (30-40 ml) and Span 85 (2 ml). Petroleum ether (30 ml) may then be added dropwise into the above dispersion. Stirring may then be continued for 2 hr. Microspheres produced in this manner will then be filtered, washed with petroleum ether and dried in a vacuum for 72 hr.

(2) o/w Emulsion method. An ultrasonified suspension of spray-dried peptide (25 mg), poly(DL-lactide/glycolide, 50:50) (Dupont or Birmingham Polymers) (0.5 g) and $CH_2CL_2$ (2 ml) will be emulsified with an aqueous solution (50 ml) containing sodium oleate (0.2 g) in a TTA-60 titration assembly for 5 min. The methylene chloride will be removed with a rotary-evaporator (120 rpm) at 360 Torr (1 h at 22° C.), 160 Torr (0.5 h at 22° C.) and 160 Torr and 40° C. (1 h). The microspheres obtained will be filtered, washed with water and vacuum dried at room temperature.

(3) (w/o)/w Emulsion method. A solution of peptide (2.6 mg) in distilled water (100 ml) will be emulsified with methylene chloride solution (0.5 g/2 ml) of poly(DL-lactide/glycolide, 50:50 Henley Chemical, RG503) through the use of a probe sonicator (Branson, Danbury, Conn.) at 125 W and 40% duty cycle, pulsed mode. This emulsion (w/o) will be emulsified in an aqueous solution (50 ml, 35° C.) containing 0.1% polyvinyl alcohol with a homogenizer (5000 rpm, ESGE Handmixer M122, Biospec Products, Bartlesville, Okla.) for 5 min. Methylene chloride will be removed from the resulting (w/o)/w emulsion on a rotary-evaporator at 300 Torr and 34° C. (120 rpm) for 1 h. The microspheres obtained will be filtered, washed with water and either vacuum dried at room temperature or lyophilized (Consol 4.5, Virtis Co., Gardiner, N.Y.).

Polymer molecular weights may be determined by gel permeation chromatography. Particle sizes of microspheres may be determined by scanning electron microscopy (SEM, Hitachi S-570, Tokyo, Japan).

In vitro peptide release studies may also be performed. Microspheres (200 mg) will be suspended in pH 7.2 phosphate-buffered saline (PBS) (2.5 ml) and agitated at 37° C. and 100 rpm in an environmental incubator shaker (G-24, New Brunswick Scientific Co., Edison, N.J.). At specific sampling times (each day for the first 4 days and every other day for the remainder of the study) the buffer solution will be completely removed and replaced with fresh PBS. The peptide content of the PBS will be measured using the Bradford method or other suitable quantitative assay.

Other methods of microencapsulation are known which may find usefulness in certain instances. See, e.g., U.S. Pat. No. 4,324,683.

II. Methods of Use

An additional embodiment of the invention is directed towards methods of using the above described hexapeptides. The methods of use preferably do not cause injury or kill normal, uninfected mammalian cells. The methods of use at therapeutic dose levels preferably do not cause injury to or kill normal uninfected mammalian cells. The methods of use may involve the use of a single hexapeptide, or may involve the use of multiple hexapeptides.

For the purposes of this invention, "active ingredient" refers to the hexapeptide with the ability to inhibit the growth of target microorganisms. Target microorganisms include but are not limited to pathogens of animals and man, such as those that cause yeast infections and various skin infections such as athlete's foot and other dermatophytic conditions. The target microorganism may also include those fungi that cause root rot, damping off, systemic infections, vascular diseases, and infections of certain surface areas of plants.

A. Animal Fungal Diseases (*Pythium, Candida*)

It is anticipated that the present invention will also find use in treating various mammalian infections. Table four below shows a variety of fungal diseases of mammals including animals and man amenable to the compositions and methods of the present invention. A pharmaceutical composition useful for treating bacterial and/or fungal infections is provided by the present invention. This pharmaceutical composition comprises an effective amount of the antimicrobial agent and a pharmaceutically acceptable carrier. Certain of the disease organisms listed here were tested with the hexapeptide compositions detailed herein. Pharmaceutically acceptable carriers are known in the art and are disclosed in The Pharmacopeia of the United States and the National Formulary in which the hexapeptides of the invention may be delivered.

TABLE 4

| FUNGUS | TARGET |
| --- | --- |
| Systemic: | |
| *Blastomyces dermatitidis* | man, dogs |
| *Coccidioides immitis* | man, dog, cattle, horse, cat, sheep, rodents(several attempts at a vaccine have been made) |
| *Histophasma capsulatum* | man, dog, cat, horse |
| *Pythium* spp. | dogs, horses |
| *Zygomycetes* spp. | Swine, goat, cattle, deer, horses, dogs, cats |
| *Rhinosporidum seeberg* | dogs, horses, man |
| *Sporothrix schenckii* | cat, dog, horse, man |
| Dermatocytes: | |
| *Microsporum canis* | cat, dog, horse, man |
| *Microsporum distortum* | Dog |
| *Microsporum gypseum* | Mammals |
| *Microsporum nanum* | Swine |

TABLE 4-continued

| | |
|---|---|
| Trichophyton mentagrophytes | dog, cat, cattle, horse, man |
| Trichophyton equinum | Horse |
| Trichophyton verrucosum | cattle, man (there is a vaccine in Europe) |
| Trichophyton gallinae | Birds |

Human Systemic Fungal Nosocomial Infections
Incidence (cases per year)

| | |
|---|---|
| Candida spp. (Species listed in descending frequency of infection causation) albicans topicalis parapsilosis krusei pseudotropicalis stellatoidea guilliermondii lusitaniae rugosa | 202,000 |
| Aspergillus spp. | 43,000 |
| Torulopsis glabrata | 18,000 |
| Zygomycetes | 7,000 |

Depending on the specific application contemplated, the pharmaceutical composition provided by the subject invention may be formulated as a solution, suspension, parental preparation, ointment, cream, lotion, spray, powder, or tablet capsule. Parental preparations may include a vehicle such as specially distilled, pyrogen-free water, phosphate buffer, or normal saline. Ointments, creams, lotions and sprays may include a carrier such as vegetable or mineral oil, white petrolatum, or a high molecular weight alcohol, i.e., greater than $C_{12}$. Tablets or capsules may include diluents, (e.g., lactose), binders, lubricants (e.g., stearic acid) and a disintegrator (e.g., corn starch).

Also provided is a method for treating a subject having a fungal infection which comprises administering to the subject an effective bacterial or fungal killing amount of the pharmaceutical composition of the present invention. Modes of administration are well recognized in the art for treatment or prevention of bacterial or fungal infections of the mucosa. Creams, suppositories or solutions which contain the active ingredient may be placed in contact with the infected area. When the infection is external, a cream may be massaged into the infected and surrounding area twice daily until after the infection has been eradicated. Where intravaginal use is required, approximately 5 grams of the cream should be injected high into the vaginal vault using a conventional applicator. This treatment should be repeated twice a day until the infection has been eradicated. Alternatively, vaginal suppositories may be inserted high into the vaginal vault once or twice daily and treatment continued until the infection has been eradicated.

It may be desirable to formulate a conventional denture adhesive paste containing an effective amount of the inventive hexapeptide or combinations thereof. Typical concentrations will range from 0.0125% to 1.5% by weight of antimicrobial agent per 100 grams of paste. Approximately 2 grams of paste is applied in the conventional manner to the contact surface of the denture prior to insertion into the mouth. Such application should be made after overnight soaking in the denture cleanser. Denture cleansers may be formulated by the addition of an effective amount of the antimicrobial agent to a tablet of approximately 3 to 3.5 grams. Such a tablet is dissolved in water yielding an antimicrobial solution for cleansing dentures. In the preferred mode of use, the denture after removal from the patient's mouth, is soaked in this cleanser for from about 8 to about 12 hours. If desired, in place of utilizing a denture cement, a denture adhesive powder can also be formulated with the antimicrobial agents of this invention.

A mouth spray containing an effective amount of the active agent may also be formulated with one or more hexapeptides of the present invention. This material may be sprayed as an antimicrobial agent in 0.25 to 0.5 ml. aliquots onto the tooth and gingiva surfaces of each quadrant between 1 and 3 times per day. In the case of denture wearers, the spray may be utilized directly on the denture surface prior to daily insertion of the denture. If desired, a mouthwash formulation may be provided containing an effective amount of the antimicrobial agent.

The antimicrobial agents may be employed in effective amounts and include doses in the range of from about 1 to about 500 mg per kilogram of host weight, when administered systemically. Active agents can be formulated in phosphate buffered saline solution. Aerosol spray inhalants are also known via which the antimicrobial hexapeptide compositions of the invention may be introduced. Exemplary methods for preparing antimicrobial peptides as pharmaceutical compositions may be found in U.S. Pat. No. 5,126,257, herein incorporated by reference in its entirety.

An embodiment of the invention is the use of one or more of the inventive hexapeptides to inhibit or kill microbial cells (microorganisms). The microorganisms may be bacterial cells, fungal cells, protozoa, viruses, or eukaryotic cells infected with pathogenic microorganisms. The method generally is directed towards the contacting of microorganisms with one or more hexapeptides of the present invention. The contacting step can be performed in vivo, in vitro, topically, orally, transdermally, systemically, or by any other method known to those of skill in the art. The contacting step is preferably performed at a concentration sufficient to inhibit or kill the microorganisms. The concentration of the hexapeptide can be at least about 0.1 µM, at least about 0.5 µM, at least about 1 µM, at least about 10 µM, at least about 20 µM, at least about 50 µM, or at least about 100 µM. The methods of use can be directed towards the inhibition or killing of microorganisms such as bacteria, gram positive bacteria, gram negative bacteria, mycobacteria, yeast, fungus, algae, protozoa, viruses, and intracellular organisms. Specific examples include, but are not limited to, *Staphylococcus, Staphylococcus aureus, Pseudomonas, Pseudomonas aeruginosa, Escherichia coli, Chlamydia, Candida albicans, Saccharomyces, Saccharomyces cerevisiae, Schizosaccharomyces pombe, Trypanosoma cruzi*, or *Plasmodium falciparum*. The contacting step can be performed by systemic injection, oral, subcutaneous, IP, IM, IV injection, or by topical application. For injection, the dosage can be between any of the following concentrations: about 1 mg/kg, about 5 mg/kg, about 10 mg/kg, about 25 mg/kg, about 50 mg/kg, about 75 mg/kg, and about 100 mg/kg. The contacting step can be performed on a mammal, a cat, a dog, a cow, a horse, a pig, a bird, a chicken, a plant, a fish, or a human.

Presently preferred hexapeptides for antibacterial applications include SEQ ID NO:1, SEQ ID NO:55, SEQ ID NO:70; SEQ ID NO:72, SEQ ID NO:79 and SEQ ID NO:80.

Presently preferred hexapeptides for antifungal applications include SEQ ID NO:1, SEQ ID NO:55, SEQ ID NO:70; SEQ ID NO:72, SEQ ID NO:79 and SEQ ID NO:80.

Presently preferred hexapeptides for antibacterial and antifungal applications include SEQ ID NO:1, SEQ ID NO:55, SEQ ID NO:70; SEQ ID NO:72, SEQ ID NO:79 and SEQ ID NO:80.

B. Synergy of Hexapeptides with Antifungals or Antibacterials

A further embodiment of the invention is directed towards methods for the additive or synergistic enhancement of the activity of a therapeutic agent. The method can comprise preparing a composition, wherein the composition comprises at least one hexapeptide of the present invention and a therapeutic agent (e.g. an antibiotic such as penicillin). Alternatively, the method may comprise co-therapy treatment with a hexapeptide (or a combination of hexapeptides) used in conjunction with other therapeutic agents. The hexapeptide or combination of hexapeptides can be any of the hexapeptides listed in Table 1. Preferably, the method comprises administering at least one of the hexapeptides of SEQ ID NO:1, SEQ ID NO:2, SEQ ID NO:3, SEQ ID NO:4, SEQ ID NO:6, SEQ ID NO:7, SEQ ID NO:55, SEQ ID NO:56, SEQ ID NO:62, SEQ ID NO:63, SEQ ID NO:69, SEQ ID NO:70, SEQ ID NO:72, SEQ ID NO:77, SEQ ID NO:78, SEQ ID NO:79, SEQ ID NO:80, SEQ ID NO:81, SEQ ID NO:83, and SEQ ID NO:84.

For example, SEQ ID NO:55 (S35-2) exhibits synergy with the therapeutic agent clotrimazole against azole resistant strains of *C. albicans*, as described in the following experiments. The fractional inhibitory concentration (FIC) index was used to determine the synergy between antimicrobial agents. Peptide MICs against test microorganisms were determined three times on separate occasions. Two-fold serial dilutions of nalidixic acid or chloramphenicol were tested in the presence of a constant amount of peptide, equal to one-quarter of the peptide MIC. The FIC index was calculated as follows: FIC=0.25+MIC (antibiotic in the combination)/MIC (antibiotic alone), where 0.25 is the ratio of the MIC of the peptide in combination with the MIC of the peptide by itself. An FIC index of less than 0.5 is considered to demonstrate synergy.

TABLE 5

Synergy Of SEQ ID NO: 55 (S35-2) With Azoles Against *C. Albicans*, FIC < 0.5 Indicate Synergistic Effects

| Strain | MIC-SEQ ID NO: 55 | MIC-clotrimazole | MIC-SEQ ID NO: 55 + azole | FIC index |
|---|---|---|---|---|
| #185 (CDR1,2) | 32 | 128 | 16/12.5 | 0.598 |
| #186 CDR1,2 | 16 | 32 | 2/12.5 | 0.515 |
| #187 CDR1,2 | 32 | >256 | 4/25 | 0.223 |
| #192 CDR1,2, | 32 | 128 | 4/50 | 0.515 |
| #196 CDR1,2 | 32 | 64 | 4/50 | 0.905 |
| #199 CDR1,2 | 32 | 64 | 4/25 | 0.515 |

All strains are azole resistant clinical isolates from Prof. Ted White (Seattle Biotechnology Research Institute, Seattle)

TABLE 6

| T.W. *Candida* | Keto-conazole | Clotrimazole | Miconazole | S35-2 SEQ ID NO: 55 | S35-3 SEQ ID NO: 56 |
|---|---|---|---|---|---|
| #184 | 64 | >256 | >256 | 32 | 128 |
| #185 | 8 | 128 | >256 | 32 | 128 |
| #186 | 8 | 32 | >256 | 16 | 128 |
| #187 | 16 | >256 | >256 | 32 | 128 |
| #192 | 32 | 128 | >256 | 32 | 128 |
| #193 | 8 | 0.5 | >256 | 32 | 128 |
| #194 | 16 | >256 | >256 | 32 | >128 |
| #195 | 128 | 256 | >256 | 64 | 128 |
| #196 | 32 | 64 | 128 | 32 | 128 |
| #197 | >256 | >256 | >256 | 32 | >128 |
| #198 | 1 | >256 | 128 | 16 | 128 |
| #199 | 16 | 64 | >256 | 32 | 128 |

In yet another example, SEQ ID NO:55 (S35-2) exhibits synergy with a therapeutic agent polymyxin B (PXB) against drug resistant bacteria such as *P. aeruginosa* such as described in Table 7. Table 7 demonstrates the potential of the hexapeptides to promote the bactericidal activity of conventional antibiotics such as polymyxin B (PXB) against drug resistant bacteria such as *P. aeruginosa*. As demonstrated, SEQ ID NO:55 (S35-2) displayed synergistic activity (indicated by an FIC index of <0.5) in combination with polymyxin B.

TABLE 7

Synergy of SEQ ID NO: 55 (S35-2) with polymyxin B (PXB)

| *P. aeruginosa* strain | MIC-1032 (ug/ml) | MIC-PXB (ug/ml) | MIC-NO: 55 combined (ug/ml) | MIC-PXB-combined (ug/ml) | FIC* |
|---|---|---|---|---|---|
| H187 | 32 | 0.5 | 8 | 0.06 | 0.37 |
| 100609 | 64 | 0.5 | 2 | 0.125 | 0.28 |
| H401 | 64 | 0.25 | 2 | 0.0625 | 0.28 |
| M917 | 64 | 1 | 16 | 0.25 | 0.266 |

Notes:
*P. aeruginosa* H187-wide type
*P. aeruginosa* 100609-tobromycin resistant
*P. aeruginosa* H401-mucoid clinical isolate
*P. aeruginosa* M917-multi-drug resistant clinical isolate
*FIC = (MIC-NO: 55-combined)/(MIC-NO: 55) + (MIC-PXB-combined)/(MIC-PXB)
*FIC < 0.5 indicates synergy The therapeutic agent can generally be any therapeutic agent, and preferably is an antibiotic, an antimicrobial agent, a growth factor, a chemotherapy agent, an antimicrobial agent, lysozyme, a chelating agent, or EDTA. Preferably, the activity of the composition is higher than the activity of the same composition containing the therapeutic agent but lacking the hexapeptide. The composition or co-therapy can be used in in vitro, in vivo, topical, oral, IV, IM, IP, and transdermal applications. The enhancement of the activity of the composition containing the therapeutic agent and the hexapeptide is preferably at least 10%, 20%, 30%, 40%, 50%, 60%, 70%, 80%, 90%, 100%, 125%, 150%, 175%, or 200% relative to the activity of the therapeutic agent alone.

Generally, any hexapeptide which is active on a stand-alone basis against a target is preferred for use to increase either additively or synergistically the activity of another therapeutic agent against that target. If several hexapeptides are candidates for a given synergy application, then the less toxic hexapeptides would be more favorably considered.

A further additional embodiment of the invention is directed towards methods for the treatment of patients diagnosed with Cystic Fibrosis (CF). CF causes, among other effects, inflammation and infection in the lungs. The above described hexapeptides of the instant invention can be used in treating such lung infections, which are often caused by *Pseudomonas aeruginosa*. The inventive hexapeptides may possess useful antimicrobial properties that would make them effective for treating lung infections in CF patients. The hexapeptide or combination of hexapeptides could be administered to a CF patient by any acceptable method including inhalation or systemic delivery. The hexapeptide or combination of hexapeptides could be administered in a single dose, in multiple doses, or as a continuous delivery.

Figure 2:
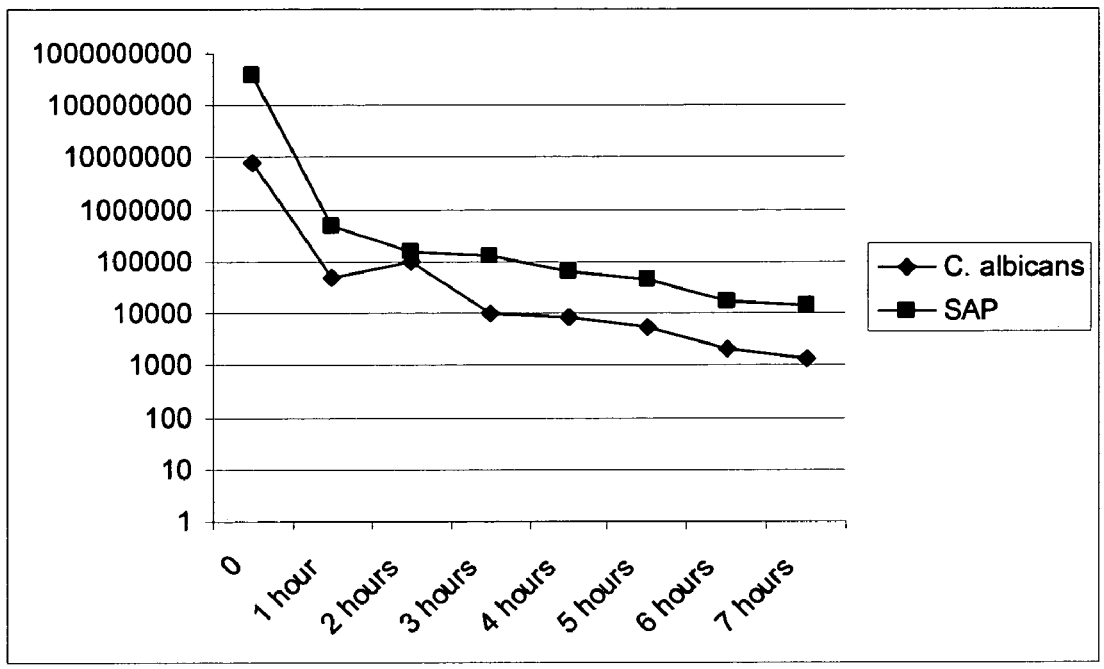
FIG. 2 shows a kill curve performed in vaginal stimulant demonstrating the killing of bacteria (*S. aureus*) and yeast (*C. albicans*) in this environment by peptide SEQ ID NO:55 (P1032).

An additional embodiment of the invention is directed towards methods of treating sexually transmitted diseases (STDs). Many of the fungal species responsible for STDs are likely to be inhibited or killed by application of one or more of the inventive hexapeptides of Table 1. Examples of such species include C. albicans, C. glabrata, and C. tropicalis. The inventive hexapeptide/s may additionally be used against other agents responsible for STDs including viruses and bacteria. The hexapeptide/s can be administered to an STD patient by any acceptable method, such as topical, oral, or systemic delivery. The hexapeptide/s can be administered in a single dose, in multiple doses, or as a continuous delivery. The hexapeptide/s can be administered in any acceptable form, such as a cream, gel, or liquid. An indication of the likelihood of activity of the hexapeptides of the present invention in the vaginal environment is shown in FIG. 2, where the activity of SEQ ID NO:55 is shown in killing curves against C. Albicans and S. aureus.

The compositions of the present invention can also include a pharmaceutically or dermatologically acceptable carrier. Examples of carriers include emulsions and gels. Emulsions are often a mixture of an oil phase and an aqueous phase. The compositions can also comprise exfoliant abrasive materials. The compositions can also comprise a stabilizer. The compositions can also comprise a foam control compound.

The compositions can also include one or more additional skin care active components. Examples of skin care active components include desquamatory actives, anti-acne actives, vitamin B3 compounds, retinoids (including retinol, retinal, retinol esters, retinyl propionate, retinoic acid, and retinyl palmitate), hydroxy acids, radical scavengers, chelators, anti-inflammatory agents, topical anesthetics, tanning actives, skin lightening agents, anti-cellulite agents, flavonoids, anti-microbial actives, skin healing agents, antifungal actives, farnesol, phytantriol, allantoin, salicylic acid, niacinamide, dexpanthenol, tocopherol acetate, and glucosamine.

The compositions can also include sunscreen compounds. Examples of sunscreen compounds include inorganic sunscreen compounds and organic sunscreen compounds. Inorganic sunscreen compounds can include metal oxides such as zinc oxide, titanium oxide, and iron oxide. Organic sunscreen compounds can include octylmethoxycinnamate, octyl salicylate, terephthalyidene dicamphor sulfonic acid, avobenzone, and octocrylene.

An additional embodiment of the invention is directed towards the use of one or more the hexapeptides of Table 1 in promoting wound healing. In certain embodiments, the hexapeptide has a high potency against microorganisms including bacteria most often associated with wound infections: S. aureus, S. pyogenes, and P. aeruginosa. Certain hexapeptide/s also promote wound healing and reduction of inflammation. The hexapeptide/s can be administered in any acceptable form, such as a cream, gel, or liquid. The hexapeptide/s can be administered in any acceptable manner, such as topical administration or systemic administration.

C. Microbial Strains

The following table lists the various microorganisms used throughout the Examples.

TABLE 8

| Microorganism | Reference or source |
|---|---|
| Escherichia coli UB1005 | D. Clark, FEMS Microb. Lett. 21: 189-195, 1984 |
| Salmonella typhimurium 14028S | Fields et al., Science 243: 1059-1062, 1989 |
| Staphylococcus aureus SAP0017 | Methicillin resistant clinical isolate from Prof. T. Chow, Vancouver General hospital |
| Pseudomonas aeruginosa H187 | Angus, et al., AAC 21: 299-309, 1982 |
| Candida albicans 105 | From Prof. Barbara Dill (UBC) |
| Pseudomonas aeruginosa 100609 | tobromycin resistant University of Calgary |
| Pseudomonas aeruginosa H401 | mucoid clinical isolate University of British Columbia |
| Pseudomonas aeruginosa M917 | multi-drug resistant clinical isolate University of British Columbia |

D. Antimicrobial Activity

MICs (minimal inhibitory concentrations) were determined for the hexapeptides of interest using a slightly modified version of the NCCLS (National Committee for Clinical Laboratory Standards) broth microdilution method as described previously (Steinberg et al., AAC 41: 1738, 1997). Briefly, antimicrobial agents were prepared as 10× concentrates in the most appropriate solvent. For the hexapeptide, 0.01% acetic acid containing 0.2% bovine serum albumin as a carrier protein was used. Inocula were prepared by resuspending colonies from a BAP (please spell out this term) in medium and adjusting the suspension to match that of a 0.5 McFarland standard. The suspension was diluted into fresh medium (as recommended by NCCLS for the organism) to give $2\times10^5$ to $7\times10^5$ CFU/ml for bacteria or $2\times10^3$ to $7\times10^3$ CFU/ml for Candida. After dispensing 100 µl aliquots of the microbial suspension into each well of a 96-well polypropylene microtiter plate, 11 µl of test compound was added. The MIC was defined as the lowest concentration of drug which prevented visible turbidity after 16 to 20 hours (bacteria) or 46 to 50 hours (Candida) at 35° C.

In Table 9, the MIC of selected hexapeptides against an extended panel of S. aureus shows their effective activity against particularly difficult clinical strains.

TABLE 9

MIC Of Hexapeptides Against Extended Panel Of S. aureus

| | Bacterial strain | | | | | | | | |
|---|---|---|---|---|---|---|---|---|---|
| Peptide | #82 | #84 | #86 | #88 | #89 | #92 | #93 | #13 | #12 |
| P1032 SEQ ID NO: 55 | 32 | 32 | 8 | 32 | 16 | 16 | 16 | 16 | 8 |
| P1033 SEQ ID NO: 56 | 32 | 32 | 4 | 16 | 16 | 16 | 16 | 32 | 8 |
| P1037 SEQ ID NO: 60 | 32 | 32 | >128 | 16 | 16 | 8 | 16 | 16 | 8 |
| P1041 | 16 | 32 | 8 | 16 | 16 | 8 | 16 | 16 | nd |
| P1081 | 16 | 16 | 8 | 16 | 8 | 8 | 8 | nd | nd |

TABLE 9-continued

MIC Of Hexapeptides Against Extended Panel Of *S. aureus*

| Peptide | Bacterial strain | | | | | | | | |
|---|---|---|---|---|---|---|---|---|---|
| | #82 | #84 | #86 | #88 | #89 | #92 | #93 | #13 | #12 |
| P1087 SEQ ID NO: 63 | 16 | 16 | 2 | 16 | 8 | 4 | 8 | 8 | 4 | nd—not determined/not assayed
Bacterial strain key:
82: *S. aureus*, burn isolate
84: MRSA
86: *S. epidermidis* ATCC12228
88: *S. aureus*, sputum isolate
89: *S. aureus* ATCC29213
92: *S. aureus*, resistant to trimethoporin
93: *S. aureus*, clinical isolate
13: *S. aureus* SAP0017, MRSA
12: *S. aureus* ATCC25923

TABLE 10

Minimal Inhibitory Concentrations (Mics)/Mg/Ml

| SEQ ID NO: | P # | Sequence (N-C) | P. aeruginosa strain H187 | S. aureus strain SAP 0017 | C. albicans strain 105 |
|---|---|---|---|---|---|
| 1 | P0666 | KFKWPW-NH$_2$ | 32 | 16 | 32 |
| 2 | P0665 | KWRWPW-NH$_2$ | 128 | 64 | 64 |
| 3 | P0736 | KWKWFW-NH$_2$ | 128 | 32-64 | 64-64 |
| 4 | P0735 | RWRWPW-NH$_2$ | >128 | 64 | 64-128 |
| 5* | P0633 | RWRWRW-NH$_2$ | 128 | 32 | 64 |
| 6 | P0734 | KFKWFW-NH$_2$ | 128 | 64 | 64 |
| 7 | P0737 | RFKWFW-NH$_2$ | 128 | 64-128 | 64-128[1] |
| 8* | P0634 | RRRWWW-NH$_2$ | >128 | >128 | >128 |
| 9* | P0635 | KFKFKF-NH$_2$ | 128 | 128 | 128 |
| 10* | P0636 | KYKYKY-NH$_2$ | >128 | >128 | >128 |
| 11* | P0637 | FKFKFK-NH$_2$ | 128 | 64 | 64 |
| 12* | P0661 | FKFKPV-NH$_2$ | >128 | >128 | >128 |
| 13* | P0662 | VKVKPV-NH$_2$ | >128 | >128 | >128 |
| 14* | P0663 | FALKKL-NH$_2$ | >128 | >128 | >128 |
| 15* | P0664 | RKTWPW-NH$_2$ | >128 | >128 | >128 |
| 16* | P0667 | FKLAPW-NH$_2$ | >128 | >128 | >128 |
| 17* | P0668 | KWKKPV-NH$_2$ | >128 | >128 | >128 |
| 18* | P0669 | FRHFRW-NH$_2$ | >128 | >128 | >128 |
| 19* | P0670 | VAKLAK-NH$_2$ | >128 | >128 | >128 |
| 20* | P0671 | FAKLAK-NH$_2$ | >128 | >128 | >128 |
| 21* | P0672 | KFKSFK-NH$_2$ | >128 | >128 | >128 |
| 22* | P0673 | KWKKLA-NH$_2$ | >128 | >128 | >128 |
| 23* | P0699 | KWKFKF-NH$_2$ | >128 | >128 | 128 |

TABLE 10-continued

Minimal Inhibitory Concentrations (Mics)/Mg/Ml

| SEQ ID NO: | P # | Sequence (N-C) | P. aeruginosa strain H187 | S. aureus strain SAP 0017 | C. albicans strain 105 |
|---|---|---|---|---|---|
| 24* | P0700 | KWKVFK-NH₂ | >128 | >128 | >128 |
| 25* | P0701 | VAKKWK-NH₂ | >128 | >128 | >128 |
| 26* | P0671 | FAKLAK-NH₂ | >128 | >128 | >128 |
| 27* | P0712 | KLAKLL-NH₂ | >128 | >128 | >128 |
| 28* | P0713 | LAKLAK-NH₂ | >128 | >128 | >128 |
| 29* | P0714 | KPWKFK-NH₂ | >128 | >128 | >128 |
| 30* | P0715 | KPVWPW-NH₂ | >128 | >128 | >128 |
| 31* | P0716 | KPVKFK-NH₂ | >128 | >128 | >128 |
| 32* | P0717 | KYVWPW-NH₂ | >128 | >128 | >128 |
| 33* | P0718 | LLKWPW-NH₂ | >128 | >128 | >128 |
| 34* | P0719 | FPWKFK-NH₂ | >128 | >128 | >128 |
| 35* | P0720 | KPVWPF-NH₂ | >128 | >128 | >128 |
| 36* | P0721 | KFFWPF-NH₂ | >128 | >128 | >128 |
| 37* | P0738 | KAKFPF-NH₂ | >128 | >128 | >128 |
| 38* | P0739 | KFKPFW-NH₂ | >128 | >128 | >128 |
| 39* | P1030 | KUKWPW-NH₂ | 128 | 64 | 32 |
| 40* | P1013 | KFKLPW-NH₂ | >128 | >128 | >128 |
| 41 | P1014 | KFKWPW-COOH | >128 | >128 | >128 |
| 42 | P1016 | KWKWPW-COOH | >128 | >128 | >128 |
| 43 | P1017 | KWKWFW-COOH | >128 | >128 | >128 |
| 44 | P1018 | KFKWFW-COOH | >128 | >128 | >128 |
| 45* | P1020 | FAKWPW-COOH | >128 | >128 | >128 |
| 46* | P1022 | VAKWPW-COOH | >128 | >128 | >128 |
| 47 | P1023 | KWKWPW-NH₂ | >128 | >128 | >128 |
| 48* | P1024 | FAKWPW-NH₂ | >128 | >128 | >128 |
| 49* | P1025 | VAKWPW-NH₂ | >128 | >128 | >128 |
| 50 | P1026 | KWKFPF-NH₂ | >128 | >128 | >128 |
| 51* | P1027 | KWKWGW-NH₂ | >128 | >128 | >128 |
| 52* | P1028 | KLKWPW-NH₂ | >128 | >128 | >128 |
| 53* | P1029 | KWKLAL-NH₂ | >128 | >128 | >128 |
| 54* | P1031 | OCT-FALLKL-NH₂ | >128 | >128 | >128 |
| 55 | P1032 | OCT-KFKWPW-NH₂ | 32 | 32 | 32 |
| 56 | P1033 | OCT-KWKWFW-NH₂ | 32 | 4 | 16 |
| 57 | P1034 | OCT-KFKWFW-NH₂ | >128 | >128 | >128 |
| 58* | P1035 | BALLKL-NH₂ | >128 | >128 | >128 |
| 59* | P1036 | KBKWPW-NH₂ | >128 | >128 | >128 |
| 60* | P1037 | KWKWBW-NH₂ | 128 | 32 | 64 |

TABLE 10-continued

Minimal Inhibitory Concentrations (Mics)/Mg/Ml

| SEQ ID NO: | P # | Sequence (N-C) | P. aeruginosa strain H187 | S. aureus strain SAP 0017 | C. albicans strain 105 |
|---|---|---|---|---|---|
| 61* | P1038 | KBKWBW-NH$_2$ | >128 | 128 | 64 |
| 62 | P1085 | KWKWUW-NH$_2$ | 16 | 8 | 64 |
| 63 | P1087 | KWKWZW-NH$_2$ | 8 | 8 | 64 |
| 64* | P1007 | KWKWLPW-NH$_2$ | 128 | 64 | 128 |
| 65* | P1008 | KWKWPPW-NH$_2$ | >128 | >128 | >128 |
| 66* | P1109 | KWKWPGW-NH$_2$ | >128 | >128 | >128 |
| 67* | P1011 | KPKWPPW-NH$_2$ | >128 | >128 | >128 |
| 68* | P1012 | KFKWPPW-NH$_2$ | >128 | >128 | >128 |
| 69 | P1145 | Hep-KFKWPW-NH$_2$ | 128 | 128 | 64 |
| 70 | P1146 | Non-KFKWPW-NH$_2$ | 32-64 | 16 | 16 |
| 71 | P1147 | Cap-KFKWPW-NH$_2$ | >128 | 128 | 128 |
| 72 | P1148 | Lau-KFKWPW-NH$_2$ | 32 | 4-8 | 8 |
| 73 | P1149 | Pal-KFKWPW-NH$_2$ | >128 | 128 | 32 |
| 74 | P1150 | Ste-KFKWPW-NH$_2$ | >128 | >128 | 128 |
| 75 | P1151 | Ole-KFKWPW-NH$_2$ | >128 | 128 | 128 |
| 76 | P1258 | Aca-KFKWPW-NH$_2$ | >128 | >128 | >128 |
| 77 | P1273 | Myr-KFKWPW-NH$_2$ | 64-128 | 8-16 | 4-8 |
| 78 | P1274 | Pen-KFKWPW-NH$_2$ | 128 | 32-64 | 8 |
| 79 | P1275 | Und-KFKWPW-NH$_2$ | 8-16 | 4 | 4-8 |
| 80 | P1276 | Tri-KFKWPW-NH$_2$ | 32 | 2-4 | 4 |
| 81 | P1205 | Oct-kfkwpw-NH$_2$ | 32 | 32 | 32 |
| 82 | P1206 | kfkwpw-NH$_2$ | >128 | >128 | >128 |
| 83 | P1343 | Lau-kfkwpw-NH$_2$ | 4 | 2 | 2 |
| 84 | P1304 | Oct-KFKWPw-NH$_2$ | 128 | 64 | 64 |
| 85 | P1345 | Deca-KFKWPW-NH$_2$ | ND | ND | ND |

*denotes non-XBXBOB hexapeptides; ND - not determined/not assayed

SEQ ID NO:5 (RWRWRW) and SEQ ID NO:8 (RRRWWW) are non-XBXBOB hexapeptides described by Strom et al. (2003). Both of these hexapeptides exhibited less activity than those of the XBXBOB family of hexapeptides of the present invention, such as SEQ ID NO:1 (PO666.). It is believed that the improved activity of the XBXBOB family of hexapeptides is due at least in part, to certain structural attributes beneficial for antimicrobial activity. Hexapeptides that do not fit within the XBXBOB formula, exhibit little or no antimicrobial activity. For optimum activity within the XBXBOB family, we have determined from structure and activity studies, that an F in position two and a P in position five is preferred within this model. We have demonstrated that the structure of F in position two may be important by substituting with a similar amino such as W, which virtually eliminated activity, see MIC data in Table 9 for SEQ ID NO: 47, (P1023)). Substituting an XBXBOB hexapeptide, that has an F at position two, with a non-natural amino acid (such as 1-naphthyl-L-alanine (denoted herein as "U"), i.e. 1-Nal, which is closer in structure to F than W is), results in intermediate activity, (see data in Table 10 for SEQ ID NO: 39 (P1030)).

E. Binding of the Bacterial Cell Wall Component Lipoteichoic Acid

Figure 7:
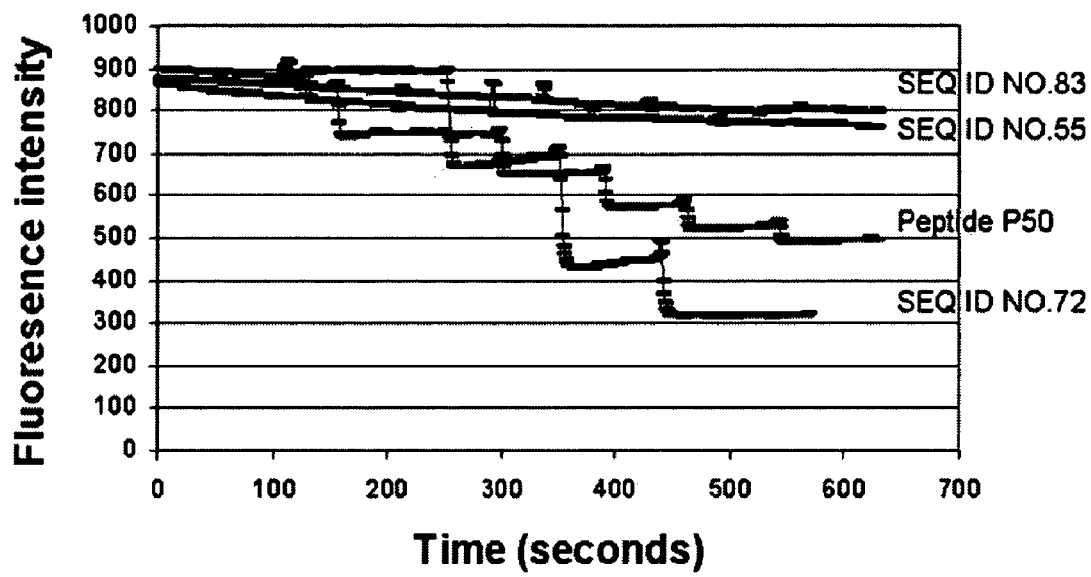
FIG. 7 shows an LTA binding assay demonstrating that SEQ ID NO:72 (P1148) binds LTA to the same degree as P50 (an active 17-mer, SEQ ID NO:88).

Lipoteichoic acid (LTA) is a common cell wall component of gram-positive bacteria including organisms such as *S. aureus* and *P. acnes*. The release of LTA during infection can lead to the release of mediators of the host inflammatory response which in turn can result in sepsis (septic shock). For example, when injected into animals, LTA can elicit many of the characteristic features of septic shock, including cytokine production, leukocytopenia, circulatory failure, multiple-organ dysfunction syndrome, and mortality. Scott et al. (Infect. And Immun. 67: 6445-6453 (1999)) demonstrated that binding of LTA by cationic peptides (26-29 residues in length) can reduce the ability of LTA to transform cells into an inflammatory response. As demonstrated in FIG. 7, the hexapeptides can be divided into two groups: (1) those peptides that do not bind LTA (SEQ ID NO:55) and (2) those peptides that do bind LTA (SEQ ID NO:72). Using the LTA binding assay described by Scott et al. (Infect. And Immun. 67: 6445-6453 (1999)) one can demonstrate (FIG. 7) that SEQ ID NO:72 binds LTA to the same degree as a typical highly charged alpha-helical amphipathic peptide such as P50 (VAKKLAK-LAKKLAKLAL-NH$_2$) SEQ ID NO:88 This is unexpected for such a short peptide and provides potential therapeutic value to certain of the hexapeptides. By contrast SEQ ID NO:83 and SEQ ID NO:55 fail to bind LTA (FIG. 7).

F. Activity Against *P. Acnes*

A very promising application for short bioactive peptides is for dermatological indications such as acne. To determine if the activity of lipo-hexapeptides was consistent across a range of *P. acnes* strains and whether that activity was comparable to the traditional longer antimicrobial peptides, ten strains (ATCC strains) of the organism were tested against SEQ ID NO:72, SEQ ID NO:55 and SEQ ID NO:81 and compared to P50 (SEQ ID NO:88). The results (Table 11) demonstrated equivalence and in some cases improvement over the longer highly charged peptide.

tionally, it appears that amidation at the C-terminus improves activity, and in some cases is required for activity. Representative examples of such hexapeptides are as follows:

```
SEQ ID NO:1: KFKWPW*** most active
SEQ ID NO:2: KWRWPW** active
SEQ ID NO:3: KWKWFW* active
```

It is apparent from the structure activity relationship (SAR) that positively charged residues in positions 1 and 3 are required for desired antimicrobial activity. It is also clear that lysine (K) may be better than arginine (R) at position 1 and optionally 3. Other combinations of residues do not provide the same activity profile as described in more detail as follows.

From the data presented in Table 10 above, it can be seen that most of the tested hexapeptides exhibit little or no antimicrobial activity. However, all of the hexapeptides of the general structure XBXBOB exhibit some desired level of antimicrobial activity. Generally, within the XBXBOB family of hexapeptides, there are two subgroups that exhibit desired activity.

Interestingly, certain hexapeptides are especially active and are considered part of subgroup 1 of the general XBX-BOB family. A representative especially active hexapeptide is

TABLE 11

| | Activity Against Extended Panel Of *P. Acnes* | | | | | | | | | |
|---|---|---|---|---|---|---|---|---|---|---|
| Peptide | ATCC 6921 | ATCC 6922 | ATCC 6923 | ATCC 11828 | ATCC 12930 | ATCC 25746 | ATCC 29399 | ATCC 33179 | ATCC 49929 | ATCC 51277 |
| P50 | 4 | 8 | 16 | 4 | 2 | 0.125 | 8 | 16 | 0.25 | 16 |
| SEQ ID NO: 72 | ND | 1 | 1 | ND | ND | 1 | 2 | 1 | ND | 1 |
| SEQ ID NO: 55 | 4 | 8 | 8 | 8 | 8 | 1 | 16 | 16 | 0.125 | 4 |
| SEQ ID NO: 81 | 4 | 8 | 8 | 8 | 2 | 0.25 | 8 | 16 | 0.125 | 8 |

Figure 8:
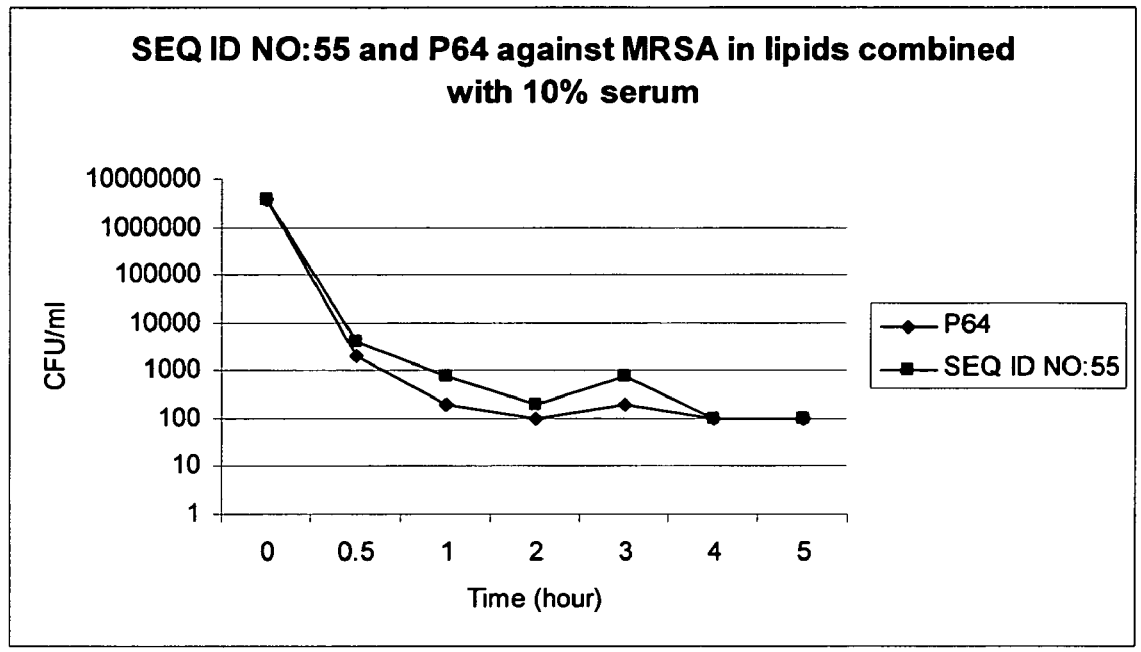
FIG. 8 shows a kill curve performed in 10% serum demonstrating the activity of SEQ ID NO:55 (P1032) compared with P64 (a traditional cationic antimicrobial peptide, SEQ ID NO:90).

Referring to FIG. 8, not only does lipidation improve the activity of hexapeptides in serum it improves activity in a lipid environment which is a mimic of the human acne lesion environment. The human sebaceous gland secretion, also called sebum, contains squalene, cholesterol, cholesterol esters, wax esters, and triglycerides in which a large follicular population follicular population of *P. acnes* appears to take advantage of this environment and hydrolyzes certain sebaceous lipids. The pre-pubertal and pubertal increase in sebum secretion is almost certainly involved in the pathogenesis of adolescent acne. The activity of SEQ ID NO: 55 was studied in this environment compared to P64(SEQ ID NO:90), a traditional cationic antimicrobial peptide. Due to the fact that most lipids are water insoluble, peptide-liposomes composed of phosphatidylcholine, phosphatidylglycerol and cholesterol in the molar ratio of 7:2:1 in saline were used and kill kinetics of the peptides were assessed in the presence or absence of serum. The bacterium used was *S. aureus* MRSA and in both settings the peptides were tested at 0.5 mg/ml concentration and shown to be effective (FIG. 8).

III. Structure and Antifungal Activity Considerations

A. XBXBOB Hexapeptides

Hexapeptides exhibiting antifungal activity adhere to the above formula where X is charged (hydrophilic), O can be a range of residues, but may preferably be a naphthylalanine, an aliphatic residue (such as proline) or an aromatic residue (such as phenylalanine) and B is a hydrophobic residue. Addi- KFKWPW-NH$_2$ (SEQ ID NO:1). Importantly, SEQ ID NO:1 is also effective and active in serum, as shown in Table 12 below. For hexapeptides within subgroup 1, activity is reduced when position two is W—for example SEQ ID NO: 47 (1023), when position five is F; for example SEQ ID NO:6 (0734), or when position two is fluorinated, for example SEQ ID NO: 59; or if position two is W while positions four and six are changed to F, for example SEQ ID NO: 50 (1026). It should be noted that the letter "J" within the sequence listing indicates a fluoronated phenylalanine.

Interestingly, adding a lipid to a representative member of subgroup 1, such as SEQ ID NO:1, does not affect the MIC but significantly increases activity in biological environments such as serum, see for example SEQ ID NO:55 (1032) and Table 12. All non-XBXBOB analogs of subgroup 1 hexapeptides are mainly inactive (see Table 12 below for specific examples).

Another subgroup of the XBXBOB hexapeptide family, designated subgroup 2, is slightly less active, but exhibits other desirable traits; a representative member of this subgroup 2 is SEQ ID NO:3 (KWKWFW-NH$_2$; (0736)). Activity of subgroup 2 members is increased by increasing the aromatic nature of residue 5 for example, SEQ ID NO: 62 and 63 have been modified by the addition of 1-Nal-OH (denoted "U" in the present sequence: listings) (1-naphthylalanine) or 2-Nal-OH (denoted "Z" in the present sequence listings)

(2-naphthylalanine), see Table 10 for activity. The abbreviation Nal is used herein to indicate either 1-Nal-OH or 2-Nal-OH.

In addition, moderate activity is gained in some cases by lipidating subgroup 2 hexapeptide members. However, unlike SEQ ID NO:55 (1032), SEQ ID NO:56 (1033) does not perform well in biological environments.

In subgroup 2 hexapeptides, activity is generally reduced by a W in position 5, an F in position 2, fluoronation of F at position 5 and any alteration that takes the sequence outside the XBXBOB formula. If position 5 is a charged residue, then in the majority of cases the peptide is relatively inactive, e.g. SEQ ID NO:9 (KFKFKF-NH$_2$), SEQ ID NO:10 (KYKYKY-NH$_2$), and SEQ ID NO:23 (KWKFKF-NH$_2$). An exception to this assertion is RWRWRW (SEQ ID NO:5) but this peptide when compared to the activities of the most active peptides such as SEQ ID NO:1, SEQ ID NO:62, SEQ ID NO:63, exhibits very low activity.

Finally, if an XBXBOB hexapeptide is non-amidated, then it is inactive e.g. SEQ ID NO:41-46, in Table 10.

TABLES 12A-B

Activity Of Short Peptides And Lipidated Version In 10% Sheep Serum-Phosphate Buffer Against MRSA

12A

|  | P0666-serum-1 mg/ml | P0666-serum-2 mg/ml | P0666-buffer-2 mg/ml | P1032-serum-0.5 mg/ml | P1032-buffer-1 mg/ml |
|---|---|---|---|---|---|
| 0 | 6$^8$ | 5$^7$ | 5$^7$ | 6$^8$ | 5$^7$ |
| 30 min | 102300 | 9800 | 99200 | 10 | 100 |
| 1 hour | 99600 | 3200 | 62800 | 10 | 100 |
| 2 hours | 15110 | 630 | 99200 | 10 | 10 |
| 3 hours | 12080 | 250 | 99200 | 10 | 10 |
| 4 hours | 5020 | 70 | 99200 | 10 | 10 |
| 5 hours | 2570 | 50 | 99200 | 10 | 10 |

12B

|  | P1032-serum-1 mg/ml | P1032-serum 2 mg/ml | Serum Control | P50-0.5 mg/ml |
|---|---|---|---|---|
| 0 | 5$^7$ | 6$^8$ | 6$^8$ | 6$^8$ |
| 30 min | 3900 | 1000000 | 6$^8$ | 38100 |
| 1 hour | 1100 | 1000000 | 6$^8$ | 37800 |
| 2 hours | 100 | 1000000 | 6$^8$ | 13340 |
| 3 hours | 30 | 1000000 | 6$^8$ | 12410 |
| 4 hours | 20 | 1000000 | 6$^8$ | 13920 |
| 5 hours | 60 | 1000000 | 6$^8$ | 11970 |

While XBXBOB hexapeptides are generally active against an array of microbial targets, not all hexapeptides are equally effective against all microorganisms. It is noted that SEQ ID NO:32-33 had poor activity against *P. auruginosa, C. albicans*, and *S. aureus* as shown in Tables 10 and 13.

Figure 3:
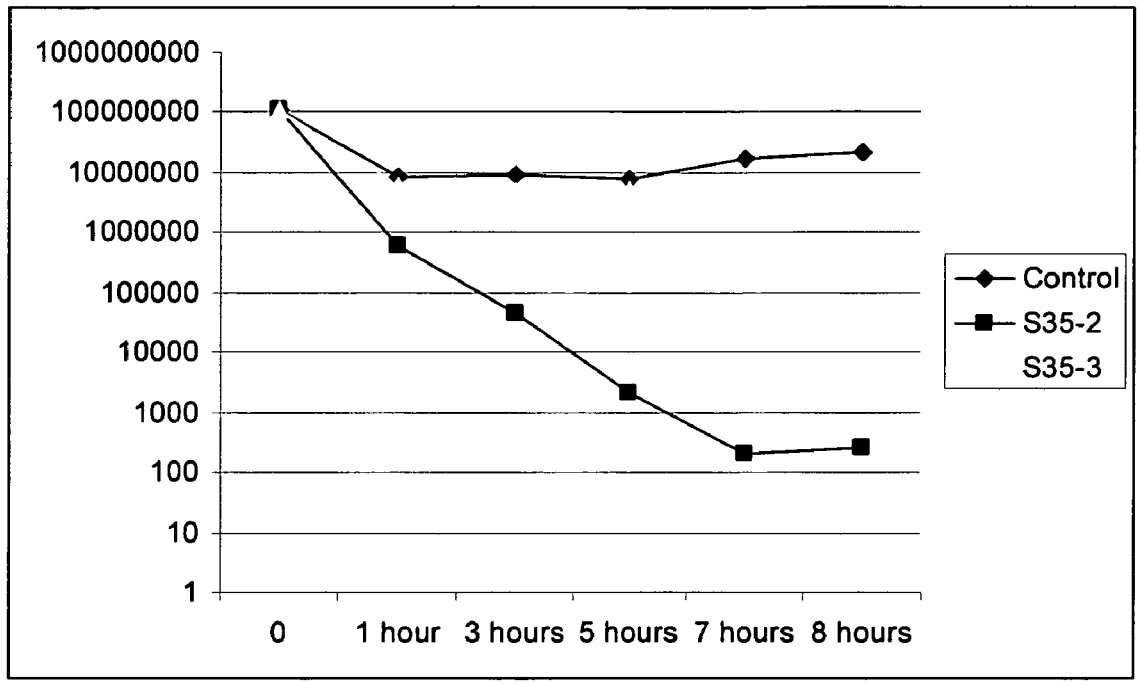
FIG. 3 shows a kill curve performed in 80% serum demonstrating the ability of SEQ ID NO:55 (P1032) to kill *S. aureus* in this environment.
Figure 4A:
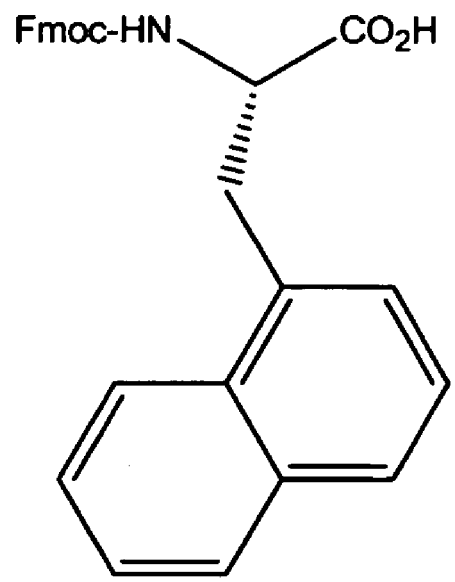
FIGS. 4A and 4B show graphical representations of the structures naphthylalanine-1 and naphthylalanine-2, demonstrating their similarity and their aromatic nature.
Figure 4B:
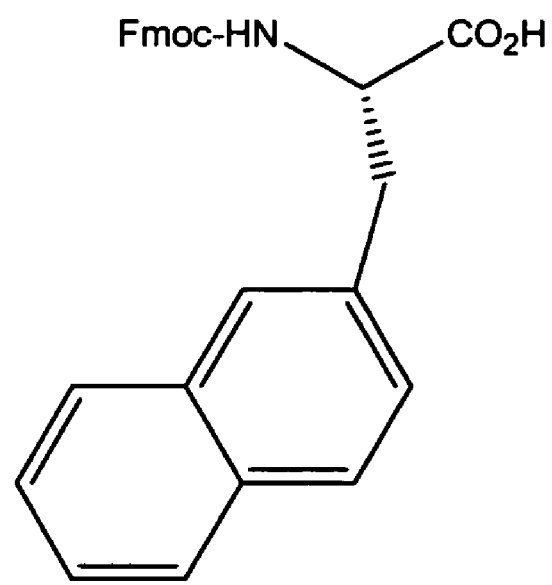
Figure 5:
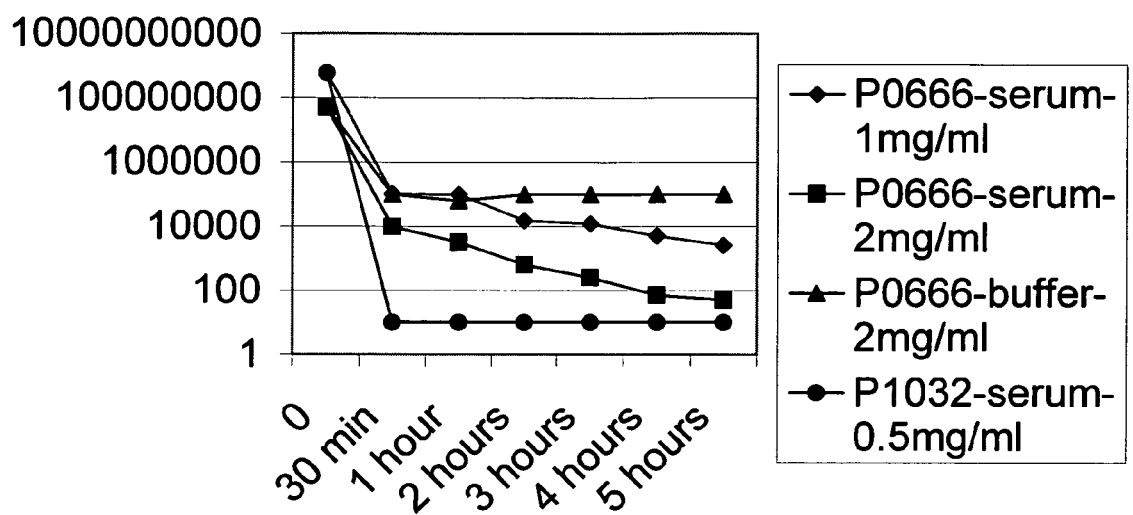
FIG. 5 shows a kill curve performed in 10% serum demonstrating the increased ability of a lipidated peptide SEQ ID NO:55 (P1032) to kill bacteria (*S. aureus*) over its non-lipidated parent SEQ ID NO:1 (P0666) in that environment.
Figure 6:
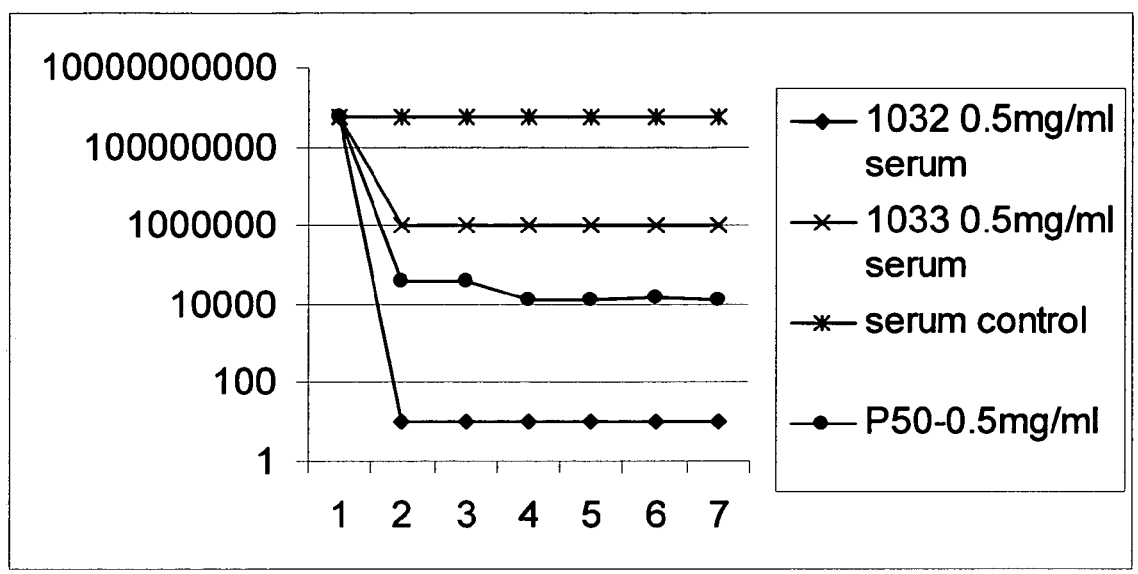
FIG. 6 shows a kill curve performed in 10% serum demonstrating the activity of SEQ ID NO:55 (P1032) compared with SEQ ID NO:56 (P1033) and P50 (an active 17-mer, SEQ ID NO:88).

Interestingly, adding a lipid to SEQ ID NO:1 (KFKWPW-NH$_2$), forming SEQ ID NO:55 (Oct-KFKWPW-NH$_2$), enhanced activity of the hexapeptide in serum, as shown in FIGS. 5-6, and Tables 9 and 12. Additionally, SEQ ID NO:55 is effective against a broad range of azole resistant clinical isolates such as *C. albicans* and *S. aureus*, as shown in Table 9, FIGS. 2-3, and FIGS. 5-6. Interestingly, SEQ ID NO:55 is also active in physiological environments such as in vaginal simulant media and in serum, as shown in FIGS. 2-3.

B. Structure Investigation of SEQ ID NO:1 (P0666)

CD spectra, shown in FIG. 1, were recorded on a model J-810 spectropolarimeter (Jasco) using a quartz cell with a 1 mm path length. Spectra were measured at room temperature between 190 nm and 250 nm at a scan speed of 50 nm/min and a total of 10 scans per sample. Spectra were recorded at a peptide concentration of 100 μg/ml in three environments: 10 mM Tris buffer, pH 7.5; 50% TFE in water; and in liposomes of POPC:POPG (1:1 w:w, 2 mM). In all cases, the peptide spectra were obtained by subtracting the spectra of the solution components in the absence of peptide.

SEQ ID NO:1 (P0666) appears to undergo a significant change in structure upon interaction with a liposomal environment, as illustrated in FIG. 1. This is in contrast to little significant change observed in buffer containing 50% TFE. A specific structure induced in a relatively short peptide is likely to a have significant bearing upon activity.

Interesting results have been obtained when substituting naphthylalanine, an alanine mimetic in some of the hexapeptides. For example, substituting the F in SEQ ID NO:1 with 1-Nal-OH (denoted "U" in the present sequence listings) (1-naphthylalanine) reduces the activity of SEQ ID NO:1. Similarly, substituting the F in SEQ ID NO:1 with 2-Nal-OH (denoted as "Z" in the present sequence listings, is the stereoisomer 2-naphthylalanine) also reduces the activity of SEQ ID NO:1. However, substituting the F in SEQ ID NO:3 with 1-Nal-OH (naphthylalanine) results in enhanced activity, and a new hexapeptide SEQ ID NO: 62 (KWKWUW-NH$_2$) where the U is 1-Nal-OH. Similar results were also obtained by substituting the F in SEQ ID NO:3 with 2-Nal-OH (a different isomer of naphthylalanine), creating SEQ ID NO:63 (KWK-WZW-NH$_2$), where Z is 2-Nal-OH. It is hypothesized that the 1-Nal-OH and 2-Nal-OH substitutions physically add bulk to the hexapeptide in the form of an extra fused aromatic ring, which also adds hydrophobicity and aromaticity to the structures, when compared to the substituted phenylalanine. Thus, it appears that bulk and or hydrophobicity are important at position 5 in SEQ ID NO:3 and the substituted SEQ ID NOs: 62 and 63, while having an adverse effect at position 2 of SEQ ID NO:1.

Figure 9:
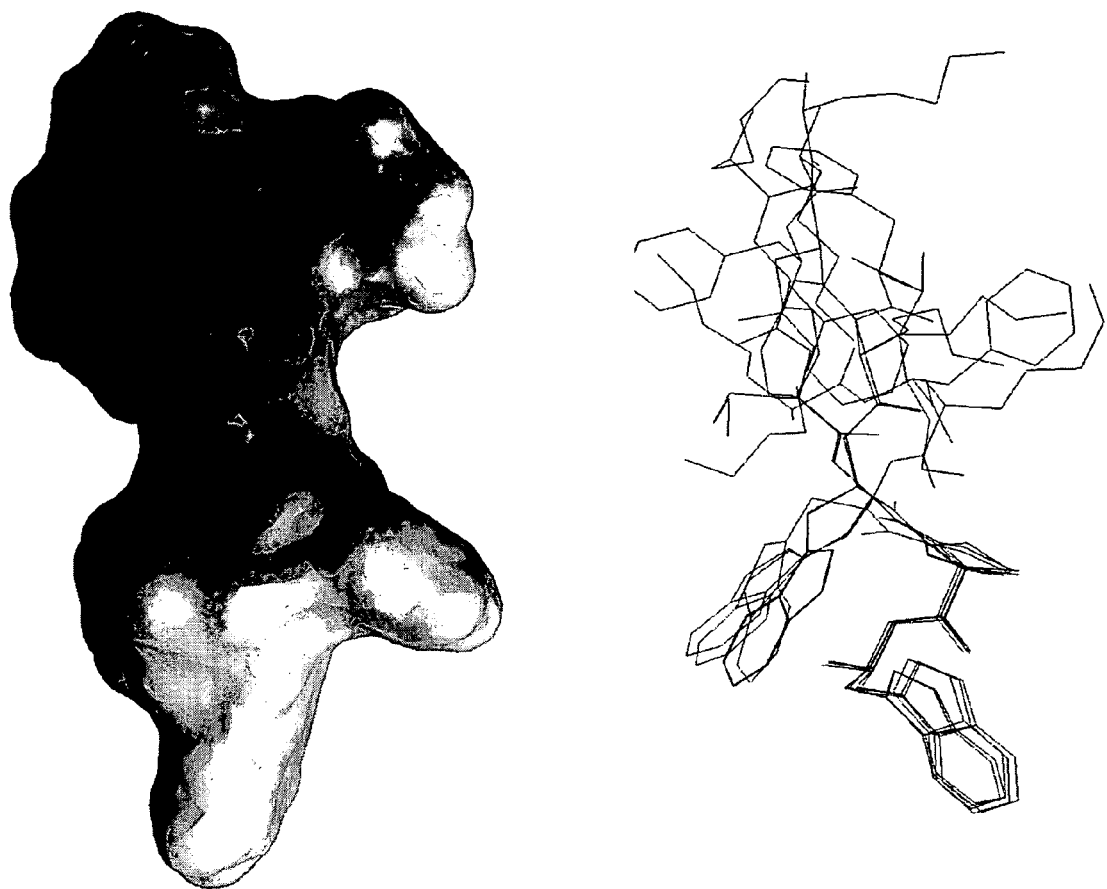
FIG. 9 represents the structure of SEQ ID NO:1 (P0666) as determined by H-NMR with charge being represented by black and hydrophobicity by white.

The solution structure of the core peptide KFKWPW-NH2 (SEQ ID NO: 1) was determined in DPC micelles by $^1$H-NMR. The structure with the lowest RMSD (root-mean-square deviation) to the mean is shown in FIG. 9 with charge being represented by blue and hydrophobicity by white. Of note is that the peptide assumes a structure which consists of a well ordered hydrophobic portion and a less ordered charged region. This amphipathicity may have significant bearing upon the peptide's activity and mechanism of action. The proline clearly plays a critical role in maintaining structure in the hydrophobic domain.

In the process of developing and studying the hexapeptides of the present invention, many examples of non-XBXBOB hexapeptides were identified, evaluated and found to exhibit little or no antimicrobial activity; these hexapeptides were generally deemed to be "non-active". Representative examples of the non-active, non-XBXBOB hexapeptides are shown in Table 13.

TABLE 13

Non-XBXBOB Hexapeptides Exhibiting Low or Absent Anti-Microbial Activity

| Peptide (SEQ ID NO:) | *E. coli* UB1005 | *S. typhimurium* 14028S | *P. aeruginosa* H374 |
|---|---|---|---|
| SEQ ID NO: 12 | >128 | >128 | >128 |
| SEQ ID NO: 13 | >128 | >128 | >128 |
| SEQ ID NO: 14 | >128 | >128 | >128 |
| SEQ ID NO: 15 | >128 | >128 | >128 |
| SEQ ID NO: 16 | >128 | >128 | >128 |
| SEQ ID NO: 17 | >128 | >128 | >128 |
| SEQ ID NO: 18 | >128 | >128 | >128 |
| SEQ ID NO: 19 | >128 | >128 | >128 |
| SEQ ID NO: 20 | >128 | >128 | >128 |
| SEQ ID NO: 21 | >128 | >128 | >128 |
| SEQ ID NO: 22 | >128 | >128 | >128 |

TABLE 13-continued

Non-XBXBOB Hexapeptides Exhibiting Low or Absent Anti-Microbial Activity

| Peptide (SEQ ID NO:) | E. coli UB1005 | S. typhimurium 14028S | P. aeruginosa H374 |
|---|---|---|---|
| SEQ ID NO: 23 | >128 | >128 | >128 |
| SEQ ID NO: 24 | >128 | >128 | >128 |
| SEQ ID NO: 25 | >128 | >128 | >128 |
| SEQ ID NO: 26 | >128 | >128 | >128 |
| SEQ ID NO: 27 | >128 | >128 | >128 |
| SEQ ID NO: 28 | >128 | >128 | >128 |
| SEQ ID NO: 29 | >128 | >128 | >128 |
| SEQ ID NO: 30 | >128 | >128 | >128 |
| SEQ ID NO: 31 | >128 | >128 | >128 |
| SEQ ID NO: 32 | >128 | >128 | >128 |
| SEQ ID NO: 33 | >128 | >128 | >128 |
| SEQ ID NO: 34 | >128 | >128 | >128 |
| SEQ ID NO: 35 | >128 | >128 | >128 |
| SEQ ID NO: 36 | >128 | >128 | >128 |

C. Structure Activity Relationship of Acylation

It has been previously demonstrated that the acylation of antimicrobial peptides can improve their activity. That improvement in activity is dependant upon the core peptide, length of attached lipid and in some cases the type of lipid attached as described by Radzishevsky et al. (Antimicrob. Agents Chemother. 49: 2412-2420 (2005)). In taking the core peptide SEQ ID NO: 1 we attached a range of lipids from 6 carbons in length to 18 including the aminoacyl group aminocaprylic acid. Attachment was performed by standard peptide chemistry methods. From this work it was demonstrated that the optimum length of an attached lipid, as it relates to antimicrobial activity is between 8 and 14 carbons Table 14). It should be noted that addition of an aminoacyl group such as aminocaprylic acid in the case of SEQ ID NO: 76 did not improve activity in contrast to peptides modified in this way described by Radzishevsky et al. (Antimicrob. Agents Chemother. 49: 2412-2420 (2005)).

Figure 10:
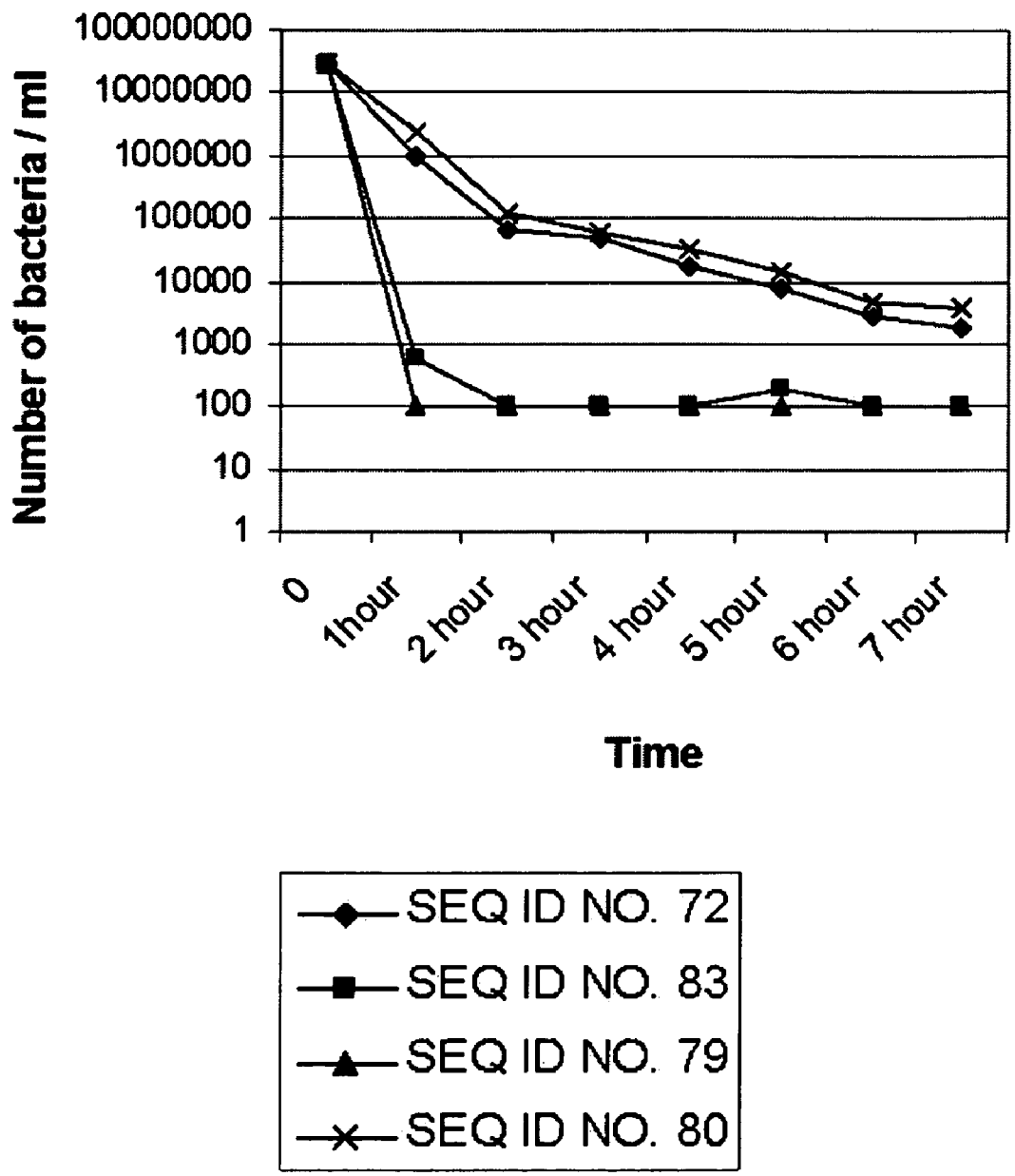
FIG. 10 shows a kill curve performed in 80% serum environment demonstrating the activity of SEQ ID NO:72 (P1148), SEQ ID NO:83 (P1343), SEQ ID NO:79 (P1275), and SEQ ID NO:80 (P1276).
Figure 11:
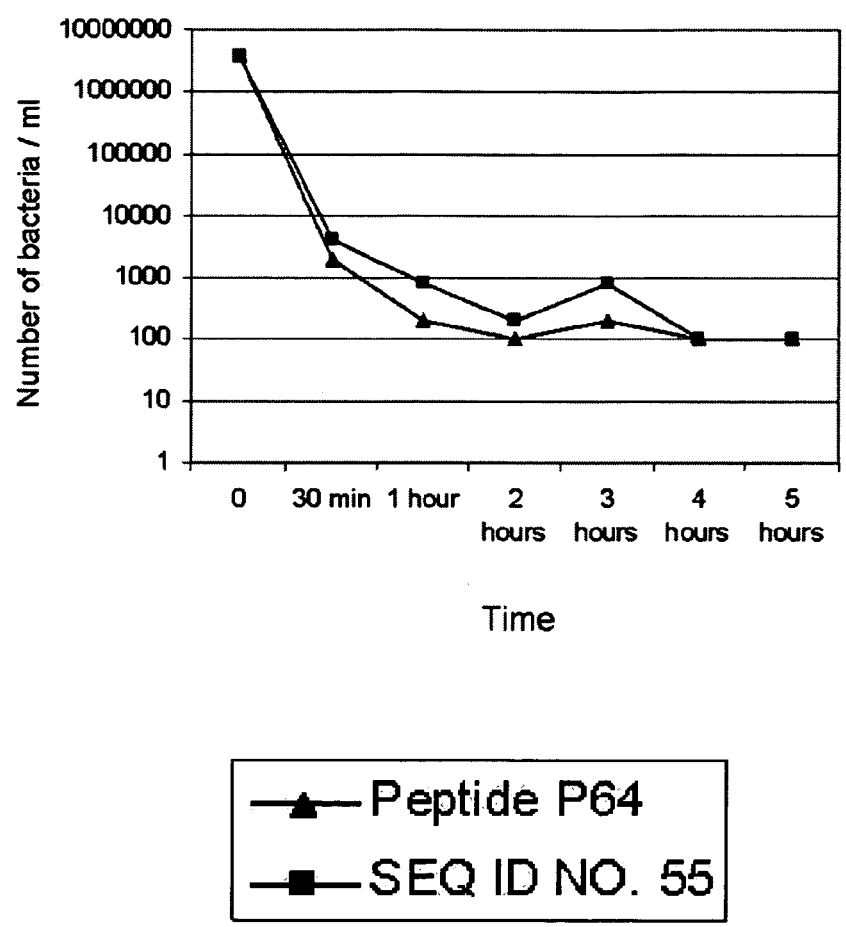
FIG. 11 shows a kill curve performed in a 1 mg/ml lipid and 10% serum environment demonstrating the activity of SEQ ID NO:55 (P1032) compared to P64 (a traditional cationic antimicrobial peptide, SEQ ID NO:90).

It should be noted that in addition to MIC data, the lipohexapeptides can also be distinguished by their ability to kill bacteria in the presence of biological constituents such as serum. Under these circumstances it can be seen that both SEQ ID NO: 79 (P1275) and SEQ ID NO: 83 (P1343) perform very well (FIG. 10). This activity, an indicator of therapeutic potential, is not obvious from the MIC data alone.

D. Mechanism of Action of Lipo-Hexapeptides

The traditional mechanism of action for antimicrobial peptides has been their ability to disrupt cell membranes. The ability of hexapeptides and lipohexapeptides to interact with lipid membranes composed of lipids that mimic either bacterial or human cells was assessed using the representative peptides SEQ ID NO: 1 (P0666) and SEQ ID NO: 55 (P1032). In these assays conventional antimicrobial peptides (15-40 amino acids in length) confer killing via the disruption of membrane bilayers causing cytoplasmic leakage resulting in cell death. To determine whether the hexapeptide P0666 and its lipidated analog P1032 follow a similar mechanism of action, they were subjected to a $diSC_35$ fluorescence de-quenching assay. $DiSC_35$ is a membrane potential sensitive dye that is taken up by energized cells according to membrane potential gradient and concentrates in the cell membrane leading to quenching of the dye fluorescence. When the membrane potential is disrupted the dye is released and is no longer quenched and thus fluorescence increases. In this case live S. aureus bacterial cells were used as the target organism. The ability of each peptide to depolarize the cytoplasmic membrane potential resulting in a loss of $diSC_35$ from cells into the buffer, and a corresponding increase in fluorescence was measured. Unlike P50 (VAKKLAKLAKKLAKLAL-$NH_2$, SEQ ID NO;88), a traditional membrane disrupting peptide, neither P0666 nor P1032 was able to cause permealization of the S. aureus cell membrane.

The lack of membrane disruption observed in S. aureus correlates well with data generated from liposome assays. Liposomes were constructed to mimic the lipid composition of either bacterial cells (POPC:POPG, 3:1) or eukaryotic cells (POPC:cholesterol, 3:1). Neither the hexapeptide or lipo-

TABLE 14

Lipid Length SAR (Structure Activity Relationship)

| SEQ ID | Lipid modification | Lipid length | P. aeruginosa | S. typhimurium | MRSA | C. albicans |
|---|---|---|---|---|---|---|
| NO:1 | Non-lipidated | 0 | 32 | nd | 16 | 32 |
| NO:71 | Cap-KFKWPW-$NH_2$ | 6 carbons | >128 | 128 | 128 | 128 |
| NO:69 | Hep-KFKWPW-$NH_2$ | 7 carbons | 128 | 128 | 128 | 64 |
| NO:55 | Oct-KFKWPW-$NH_2$ | 8 carbons | 32 | 32 | 16 | 32 |
| NO:70 | Non-KFKWPW-$NH_2$ | 9 carbons | 32-64 | 16 | 16 | 16 |
| NO:79 | Und-KFKWPW-$NH_2$ | 11 carbons | 8-16 | 8-16 | 4 | 4-8 |
| NO:72 | Lau-KFKWPW-$NH_2$ | 12 carbons | 32 | 32 | 4-8 | 8 |
| NO:80 | Tri-KFKWPW-$NH_2$ | 13 carbons | 32 | 32-64 | 2-4 | 4 |
| NO:77 | Myr-KFKWPW-$NH_2$ | 14 carbons | 64-128 | >128 | 8-16 | 4-8 |
| NO:78 | Pen-KEKWPW-$NH_2$ | 15 carbons | 128 | >128 | 32-64 | 8 |
| NO:73 | Pal-KFKWPW-$NH_2$ | 16 carbons | >128 | >128 | 128 | 32 |
| NO:75 | Ole-KFKWPW-$NH_2$ | 17 carbons | >128 | >128 | 128 | 128 |
| NO:74 | Ste-KFKWPW-$NH_2$ | 18 carbons | >128 | >128 | >128 | 128 | hexapeptide at 4 ug/ml caused dye (cacein) to be released from liposomes (POPC:POPG, 3:1) as opposed to P50 (SEQ ID NO;88) at 2 ug/ml. Both hexapeptides did not cause significant amount of calcein release even at 128 ug/ml from liposomes (POPC:cholesterol, 3:1).

E. Resistance Emergence

With a novel mechanism of action resistance emergence should always be a concern. MRSA (strain SAP0017) and *S. aureus* (strain ATCC 21923) were serially transferred daily in the presence of half-MIC concentrations of P1032 and P1032d. After 30 serial passages the MIC changes were within 2-two dilutions of the starting MIC. Such resistance was demonstrated to be transient adaptation, since a single passage of each resistant strain in the absence of peptide resulted in reversion to original MIC.

The following examples are included to demonstrate preferred embodiments of the invention. It should be appreciated by those of skill in the art that the techniques disclosed in the examples which follow represent techniques discovered by the INVENTORS to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the scope of the invention.

F. Minimum Inhibitory Concentration (MIC) Evaluation of Antimicrobial Hexapeptides Against Dermatophytes *Trychophyton Rubrum* and *Trychophyton Mentagrophytes*

In order to compare the activity of various antimicrobial peptides, including hexapeptide SEQ ID NO:1 (P0666), MIC were determined against the dermatophytes *Trychophyton rubrum* and *Trychophyton mentagrophytes*. The concentration of samples investigated were: 2000, 1000, 500, 250 and 125 μg/ml, respectively. The medium used was modified Sabouraud's media without agar. For a 100 mL of modified Sabouraud medium: 3 g of Sabouraud's dextrose broth (Difco) was mixed into 100 mL of deionized water. The pH was adjusted to 7.0 with 0.1 N NaOH. The solution was autoclaved for thirty minutes. 940 μL of medium was poured into sterile 20 mL test tubes with plastic caps and was allowed to cool.

50 μL of saline was added to each 20 mL test tube to make the required concentration. A control tube was composed of 50 μL of saline without sample. For the MIC experiments, 10 μL of organism suspended in saline was added to the each 20 mL test tube and vortexed slightly. Each of the test tubes was covered in parafilm and maintained on a shaker at 27° C. at a speed of approximately 100 rpm.

The growth/inhibition of the organism was observed on a daily basis. Growth of the organisms was observed on the fifth and tenth day and is shown in Table 12. The MIC experiment was repeated at 125 ppm, since the growth of most organisms was inhibited on the fifth day at 250 ppm. The Minimum Inhibition Concentration ($MIC_{100}$) for compounds F1 to F10 against fungus *Trychophyton rubrum* and *Trychophyton mentagrophytes* at 10 days.

TABLE 15

| $MIC_{100}$ (ug/ml) | | |
|---|---|---|
| T. rubrum | T. mentagrophytes | Peptide |
| 1000 | 250 | P153 FALKALKKILKKALKKAL-NH$_2$ (SEQ ID NO:86) |
| 500 | 500 | P55 FAKLLAKALKKLL-NH$_2$ (SEQ ID NO:87) |

TABLE 15-continued

| $MIC_{100}$ (ug/ml) | | |
|---|---|---|
| T. rubrum | T. mentagrophytes | Peptide |
| 500 | 500 | P50 VAKKLAKLAKKLAKLAL-NH$_2$ (SEQ ID NO:88) |
| 500 | 500 | P43 FAKLLAKLAKKLL-NH$_2$ (SEQ ID NO:89) |
| 1000 | 500 | P64 FAKALKALLKALKAL-NH$_2$ (SEQ ID NO:90) |
| 250 | 250 | P0666 (SEQ ID NO:1) KFKWPW-NH$_2$ |

SEQ ID NO:1 (P0666 KFKWPW-NH$_2$) was found to be the most active against *T. rubrum and T. mentagrophytes*. There was only a slight growth at 125 ppm on day ten.

G. Toxicity Testing

In order to evaluate the potential toxic effects of systemic administration of the hexapeptides of the present invention, a range of peptides exhibiting antifungal activity was introduced into the blood system of a mouse by tail vein injection at a dosage of 20 mg/Kg. As seen from the data below in Table 13, SEQ ID NO:1 (Ref. P0666; KFKWPW-NH$_2$), unlike the other tested peptides, did not elicit systemic toxicity.

TABLE 16

| SEQ ID NO (ref. Name) | Compound Dose | Solvent | Route | Result |
|---|---|---|---|---|
| SEQ ID NO: 1 (P0666) KFKWPW-NH$_2$ | 20 mg/kg | water | IV | No adverse effects |
| SEQ ID NO:55 (P01032) Oct-KFKWPW-NH$_2$ | 80 mg/kg | Saline | IV | No adverse effects |
| SEQ ID NO:86 (P153) FALKALKKLKKALK KAL-NH$_2$ | 20 mg/kg | water | IV | Reduced motor activity |
| SEQ ID NO:91 (P650) FAKALLKALLKALK-NH$_2$ | 20 mg/kg | ringers | IV | ⅓ dead clinical problems |
| SEQ ID NO:92 (P146) KYKKALKKLAKLL-NH$_2$ | 20 mg/kg | ringers | IV | ⅔ dead |

H. Cytotoxicity Studies

1. In Vivo Activity of P01032

Samples of SEQ ID NO:55 (S35-2) at a concentration of 0.1 mg/ml and at 0.5 mg/ml were tested for cytotoxicity and were found to be non cytotoxic in tests of 24 and 48 hours, where cell confluency, crenation, vacuolization, and cytolysis were evaluated.

Previous studies have documented that antimicrobial peptide P-50 (a 17-mer) has prophylactic benefit in reducing bacterial contamination by *S. aureus* from the surface of partial-thickness wounds. SEQ ID NO:55 (P-1032) has also demonstrated similar antimicrobial activity in vitro.

A study to evaluate the in vivo antimicrobial activity of SEQ ID NO:55 (P-1032) compared to P-50 was conducted with the following parameters. All test agents were supplied by Helix BioMedix, Inc. In this study two treatment groups were evaluated:

I. 1% P-50 peptide contained in a 4% HEC solution; and
II. 1% SEQ ID NO:55 (P-1032) peptide contained in a 4% HEC gel.

Both test agents were transferred to 3 ml syringes using aseptic technique. During the study 0.5 ml of the appropriate agent was dispensed to each wound. This amount covered the entire wound surface with a thin layer of solution or gel. The test bacteria was *S. aureus* (ATCC 12600). The results of these studies are shown in Tables 14-16

Twelve Sprague-Dawley, female rats (250-280 g) were anesthetized and prepared for surgery. On the back of each rat a 1"×1" partial-thickness skin wound was created with a Brown Dermatome. Each wound was contaminated with $3.1 \times 10^5/0.05$ ml of *S. aureus* (LOG 5.49). The wounds were allowed to dry for 30 minutes before the animals were divided equally into 4 treatment groups. The wounds in each group received 0.5 ml of the appropriate test agent. Each wound was covered with a transparent film dressing, covered with a gauze pad, and secured with adhesive tape.

Twenty-four hours following the first treatment the animals were anesthetized and their bandages removed. The wound surface was gently cleaned with moist gauze and a new aliquot (0.5 ml) of topical agent applied. The animals were rebandaged as described previously.

A dressing change and reapplication of the topical agent was performed again at 48 hours. Thus each animal received 3 topical treatments.

Seventy-two hours after surgery the rats were euthanized and a full-thickness, 8 mm punch biopsy was obtained from the center of the wound. The biopsy was placed in a pre-weighed tube containing 5 ml of sterile saline and reweighed to determine the sample weight. Using a tissue grinder the biopsy was homogenized and serially diluted and plated to determine the number of bacteria per gram of tissue.

Eighteen hours prior to surgery, a single colony of *S. aureus* was transferred by a sterile loop from a stock plate to trypticase soy broth. The broth culture was agitated in a water bath of 37° C. for 18 hours before collecting the bacteria by centrifugation at 3200 rpm for 10 minutes. The bacterial pellet was washed twice in a sterile 0.9% saline solution and again collected into a pellet by centrifugation. The pellet was resuspended in 2 ml sterile saline and thoroughly mixed to produce a stock solution. A series of 1:10 dilutions, ranging from $10^{-1}$ to $10^{-8}$ was then prepared from the stock solution. Standard plating techniques were used to quantitate the number of bacteria in the stock solution and subsequently each 1:10 dilution. The inoculum used was calculated to be $3.1 \times 10^5$ CFU/0.05 ml (LOG 5.49). The inoculum tube was kept on ice, and gently agitated and drawn into a sterile pipette tip immediately prior to use.

Twelve, female, Sprague-Dawley rats (250-280 g) were used. They were anesthetized intramuscularly with a mixture of ketamine (50 mg/kg) and xylazine (10 mg/kg). Their dorsal hair was clipped with electric clippers and the skin depilated with Nair. A 1"×1" template was traced on the center of the back using an alcohol-resistant marker. The skin was then prepared with iodophor scrub, followed by a 70% isopropyl alcohol, iodophor solution, and 70% alcohol. Shur-Clens was wiped on the graft area and dermatome for lubrication. Then a standard partial-thickness skin graft (0.015" thickness) was removed in the 1"×1" marked area, using an air-driven Brown Dermatome.

After hemostasis was achieved with dry gauze, an Eppendorf pipetter was used to apply exactly 0.05 ml of the inoculum to each wound. The wounds were allowed to dry for 30 minutes before each wound received 0.5 ml of topical agent. Each wound was then covered with a transparent wound dressing (Teqaderm, 3M, St. Paul, Minn.). The animals were bandaged with sterile gauze and 2 circumferential wraps of 3" cloth tape. They were given Buprenorphine analgesia and recovered from anesthesia and returned to standard housing and care.

At 24 and 48 hours after surgery, all rats were reanesthetized by Isofluorane inhalation and their bandages removed. The dressings were carefully removed and any fluid present was blotted with sterile gauze. A 0.5 ml aliquot of the designated treatment gel was then applied evenly to the entire wound surface, and the animals were redressed and recovered the same as at surgery.

2. Analysis of Wound Appearance

Each wound observed at each dressing change and the wound surface and tissue reaction assessed. There were 5 parameters of wound status that were checked:

i. Wound Film Security—Was the adhesive film used to cover the wound still completely adherent to the skin around the wound?

ii. Wound Surface—What was the exact visual appearance of the wound surface?

iii. Amount of Exudate—How much exudate was trapped under the film? In many cases, accumulated exudate causes the film to lose adherence and the exudates will escape.

iv. Severity of Tissue Reaction—A subjective rating of extent of tissue reaction on a scale of 1 (minimal), 2 (moderate), 3 (extensive).

v. % of Tissue Involved—In some situations, the wound surface contained denatures, friable tissue that could be wiped off with pressure applied to gauze. This test was used to better differentiate denatured tissue from viscous exudates.

3. Evaluation of Bacterial Counts

At 72 hours after surgery, the rats were euthanized, their dressings removed, and a 8 mm, full-thickness, punch biopsy was taken from the center of each wound and placed into a preweighed tube containing 5 ml of sterile saline. The tubes containing the samples were reweighed and the sample weights determined. The samples were homogenized and then serially diluted 4 times and plated on trypticase soy agar. The plates were incubated overnight, and the colonies were counted, and the bacterial counts per gram of tissue were calculated and converted to base 10 logarithm. The mean and standard deviation of each group were calculated and an ANOVA (Analysis of Variance) was used to determine any significant differences between the three treatment groups.

4. Postoperative Complications

All animals survived the study without complications.

No bacteria were detected in 11 of 12 treated wounds (Tables 17-18). On one wound treated with 1% P-50, a few *S. aureus* were detected (Table 18).

5. Tissue Reaction

In general, the tissue reaction to peptide SEQ ID NO:55 (P-1032) was mild, while that to P-50 was mild to moderate (as shown in the results of Table 19).

6. Results Summary

1% SEQ ID NO:55 (P-1032) in 4% HEC appears to provide the same level of antimicrobial action against *S. aureus* (ATCC 12600) as 1% P-50 (Tables 17-18).

TABLE 17

LOG INNOCULUM = 5.49
*S. aureus* (ATCC 12600)
I. - 1% P-50 in 4% HEC

| An # | LOG/cm² | tissue wt (g) | LOG/g |
|---|---|---|---|
| 1 | 1.70 | 0.1886 | 2.42 |
| 3 | 1.70 | 0.1821 | 2.44 |
| 5 | 1.70 | 0.1694 | 2.47 |
| 7 | 1.70 | 0.2000 | 2.40 |
| 9 | 2.81 | 0.1428 | 3.66 |
| 11 | 1.70 | 0.1905 | 2.42 |
| MEAN | 1.89 | 0.1789 | 2.64 |
| s.d. | 0.45 | 0.0204 | 0.50 |

Note:
All samples except #9 had log counts indicating no visible growth for that sample, or the minimal limit of detection of bacteria.
An # = animal number.

TABLE 18

II. - 1% SEQ ID NO: 55 (P-1032) in 4% HEC

| An # | LOG/cm² | tissue wt (g) | LOG/g |
|---|---|---|---|
| 2 | 1.70 | 0.1493 | 2.53 |
| 4 | 1.70 | 0.1859 | 2.43 |
| 6 | 1.70 | 0.1889 | 2.42 |
| 8 | 1.70 | 0.1956 | 2.41 |
| 10 | 1.70 | 0.1905 | 2.42 |
| 12 | 1.70 | 0.1422 | 2.55 |
|  | 1.70 | 0.1754 | 2.46 |
|  | 0.00 | 0.0233 | 0.06 |

TABLE 19

TISSUE REACTION

| GROUP | ANIMAL # | Unsealed film | Amount of exudate Day 1 | Day 2 | Day 3 | Wound aspect Day 1 | Day 2 | Day 3 | Tissue reaction severity Day 1 | Day 2 | Day 3 | % Tissue removed Day 1 | Day 2 | Day 3 |
|---|---|---|---|---|---|---|---|---|---|---|---|---|---|---|
| I. | 1 | Y | — | — | — | S/y | 2/y | 2/y | 1 | 2 | 2 | — | — | — |
| 1% P-50 | 3 | — | — | — | S/y | S/y | S/y | 2/y | 2/y | 2/y | 1 | 2 | 2 | — | — | — |
|  | 5 | — | — | — | S/y | S/y | S/y | 2/y | 2/y | 2/y | 1 | 2 | 2 | — | — | — |
|  | 7 | — | — | S/y | — | S/y | 2/y | 2/y | 2/y | 1 | 2 | 1 | — | — | — |
|  | 9 | — | — | — | — | S/y | S/y | 2/y | 2/y | 2/y | 1 | 2 | 2 | — | — | — |
|  | 11 | Y | — | — | S/y | S/y | S/y | 1 | 1 | 1 | 1 | 1 | 1 | — | — | — |
| II. | 2 | — | — | — | — | S/y | S/y | 1 | 1 | 2/y | 1 | 1 | 1 | — | — | — |
| 1% SEQ ID NO: 55 (P-1032) | 4 | Y | — | — | — | S/y | S/y | 1 | 1 | 1 | 1 | 1 | 1 | — | — | — |
|  | 6 | — | — | — | L/b | S/y | S/y | 1 | 2/w | 2/y | 1 | 1 | 1 | — | — | — |
|  | 8 | — | — | — | — | S/y | S/y | 1 | 1 | 2/y | 1 | 1 | 1 | — | — | — |
|  | 10 | — | — | — | — | S/y | S/y | 1 | 1 | 1 | 1 | 1 | 1 | — | — | — |
|  | 12 | — | — | — | — | S/y | S/y | 1 | 1 | 1 | 1 | 1 | 1 | — | — | — |
| DAY |  |  | 1 | 2 | 3 | 1 | 2 | 3 | 1 | 2 | 3 | 1 | 2 | 3 |

Observation Key:
Unsealed film: Y = yes; — = no
Wound Aspect: 1 = normal; 2 = some areas showing tissue reaction; 3 = remarkable denatured tissue; y = yellowish; r = reddish; b = brown
Amount of exudate: — = nothing; S = small; L = large
Tissue reaction severity: 1 = minimal; 2 = middle; 3 = Large All of the COMPOSITIONS and/or METHODS and/or PROCESSES disclosed and claimed herein can be made and executed without undue experimentation in light of the present disclosure. While the COMPOSITIONS and METHODS of this invention have been described in terms of preferred embodiments, it will be apparent to those of skill in the art that variations may be applied to the COMPOSITIONS and/or METHODS and in the steps or in the sequence of steps of the METHODS described herein without departing from the concept and scope of the invention.

What is claimed is:

1. A hexapeptide comprising the amino acid sequence given by the formula XBXBOB, wherein X is selected from the group consisting of Arginine (R) and Lysine (K); B is selected from the group consisting of Phenylalanine (F) and Tryptophan (W); and O is selected from the group consisting of naphthylalanine (Nal), Proline (P), and Phenylalanine (F).

2. The hexapeptide of claim 1, wherein naphthylalanine (Nal) is 1-Nal-OH (U) or 2-Nal-OH (Z).

3. The hexapeptide of claim 2, wherein the hexapeptide is selected from the group consisting of KFKWPW-NH$_2$ (SEQ ID NO:1), KWRWPW-NH$_2$ (SEQ ID NO:2), KWKWFW-NH$_2$ (SEQ ID NO:3), RWRWPW-NH$_2$ (SEQ ID NO:4), KFKWFW-NH$_2$ (SEQ ID NO:6), RFKWFW-NH$_2$ (SEQ ID NO:7), OCT-KFKWPW-NH$_2$ (SEQ ID NO:55), OCT-KWK-WFW-NH$_2$ (SEQ ID NO:56), KWKWUW-NH$_2$ (SEQ ID NO:62), and KWKWZW-NH$_2$ (SEQ ID NO:63).

4. The hexapeptide of claim 1, wherein the hexapeptide is SEQ ID NO:1.

5. The hexapeptide of claim 1, wherein said hexapeptide is modified.

6. The hexapeptide of claim 5, wherein said hexapeptide is modified with a lipid or amide group.

7. The hexapeptide of claim 6, wherein the lipid is selected from the group consisting of heptanoic acid, nonanoic acid, lauric acid, myristic acid, decanoic acid, pentadecanoic acid, undecanoic acid, tridecanoic acid, and octanoic acid.

8. The hexapeptide of claim 7, wherein the hexapeptide is selected from the group consisting of Hep-KFKWPW-NH$_2$ (SEQ ID NO:69), Non-KFKWPW-NH$_2$ (SEQ ID NO:70), Lau-KFKWPW-NH$_2$ (SEQ ID NO:72), Myr-KFKWPW-NH$_2$ (SEQ ID NO:77), Pen-KFKWPW-NH$_2$ (SEQ ID NO:78), Und-KFKWPW-NH$_2$ (SEQ ID NO:79), Tri-KFKWPW-NH$_2$ (SEQ ID NO:80), Oct-kfkwpw-NH$_2$ (SEQ ID NO:81), Lau-kfkwpw-NH$_2$ (SEQ ID NO:83), Oct-KFKWPw-NH$_2$ (SEQ ID NO:84) and Deca-KFKWPW-NH$_2$ (SEQ ID NO:85).

9. A composition comprising the hexapeptide of claim 1 and a pharmaceutically acceptable carrier.

10. The composition of claim 9, wherein said hexapeptide is soluble in an aqueous solution.

11. The composition of claim 9, wherein said hexapeptide is present in an effective concentration ranging from about 0.0002% to about 90% by weight.

12. The composition of claim 11, wherein said effective concentration is in the range of about 0.5% to about 10% by weight.

13. The composition of claim 9, which is in the form of a solution, cosmetic preparation, powder, emulsion, lotion, spray, ointment, aerosol, cream or foam.

14. The composition of claim 9, wherein the hexapeptide is modified with a lipid or amide group.

15. The composition of claim 14, wherein the lipid is selected from the group consisting of heptanoic acid, nonanoic acid, lauric acid, myristic acid, decanoic acid, pentadecanoic acid, undecanoic acid, tridecanoic acid, and octanoic acid.

16. A method of treating or preventing microbial infections in mammals, said method comprising administering to said mammal a therapeutically effective amount of the hexapeptide of claim 1.

17. The method of claim 16, wherein the microbial infection is a fungal infection, a bacterial infection, or a mixed fungal and bacterial infection.

18. The method of claim 17, wherein the fungal infection is caused by a fungus selected from the group consisting of *Candida albicans, Trichophyton rubrum,* and *Trichophyton mentagrophytes.*

19. The method of claim 17, wherein the bacterial infection is caused by a bacterium selected from the group consisting of *P. aeuroginosa, E. coli,* and *S. aureus.*

20. A method of inhibiting the growth of a fungal cell comprising:
contacting said fungal cell with an effective amount of a hexapeptide of claim 1 such that growth of the fungal cell is inhibited.

21. A method of inhibiting the growth of a fungal cell comprising:
contacting said fungal cell with an effective amount of a hexapeptide comprising the amino acid sequence given by the formula XBXBOB; wherein X is a charged residue, B is a hydrophobic residue, and O is a naphthylalanine, an aliphatic, or an aromatic residue; and wherein said fungal cell is a plant pathogen selected from the group consisting of *Mycosphaerella brassicicola, Pyrenopeziza brassicae, Peronospora destructor,* and *Botrytis squamosa.*

22. A method of inhibiting the growth of a fungal cell comprising:

contacting said fungal cell with an effective amount of a hexapeptide comprising the amino acid sequence given by the formula XBXBOB; wherein X is a charged residue, B is a hydrophobic residue, and 0 is a naphthylalanine, an aliphatic, or an aromatic residue; and wherein said fungal cell is selected from the group consisting of *Trichophyton rubrum,* and *Trichophyton mentagrophytes.*

23. The hexapeptide of claim 1, wherein the hexapeptide is SEQ ID NO:72.

24. The hexapeptide of claim 1, wherein the hexapeptide is SEQ ID NO:79.

25. The hexapeptide of claim 1, wherein the hexapeptide is SEQ ID NO:85.

26. The method of claim 20, wherein the hexapeptide is selected from the group consisting of SEQ ID NO:1, SEQ ID NO:72, SEQ ID NO:79 and SEQ ID NO:85.

* * * * *

UNITED STATES PATENT AND TRADEMARK OFFICE
CERTIFICATE OF CORRECTION

PATENT NO. : 7,407,940 B2 Page 1 of 1
APPLICATION NO. : 11/350192
DATED : August 5, 2008
INVENTOR(S) : Timothy J. Falla, Lijuan Zhang and Scott M. Harris It is certified that error appears in the above-identified patent and that said Letters Patent is hereby corrected as shown below:

Column 83, Line 6 (claim 22): delete "0" and enter -- O --.

Signed and Sealed this

Twenty-third Day of September, 2008

JON W. DUDAS
*Director of the United States Patent and Trademark Office*

```
                         SEQUENCE LISTING

<160> NUMBER OF SEQ ID NOS: 85

<210> SEQ ID NO 1
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (6)..(6)
<223> OTHER INFORMATION: AMIDATION

<400> SEQUENCE: 1

Lys Phe Lys Trp Pro Trp
1               5

<210> SEQ ID NO 2
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (6)..(6)
<223> OTHER INFORMATION: AMIDATION

<400> SEQUENCE: 2

Lys Phe Lys Trp Pro Trp
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (6)..(6)
<223> OTHER INFORMATION: AMIDATION

<400> SEQUENCE: 3

Lys Phe Lys Trp Pro Trp
1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (6)..(6)
<223> OTHER INFORMATION: AMIDATION

<400> SEQUENCE: 4

Arg Trp Arg Trp Pro Trp
1               5
```

<210> SEQ ID NO 5
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (6)..(6)
<223> OTHER INFORMATION: AMIDATION

<400> SEQUENCE: 5

Arg Trp Arg Trp Arg Trp
1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (6)..(6)
<223> OTHER INFORMATION: AMIDATION

<400> SEQUENCE: 6

Lys Phe Lys Trp Phe Trp
1               5

<210> SEQ ID NO 7
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (6)..(6)
<223> OTHER INFORMATION: AMIDATION

<400> SEQUENCE: 7

Arg Phe Lys Trp Phe Trp
1               5

<210> SEQ ID NO 8
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (6)..(6)
<223> OTHER INFORMATION: AMIDATION

<400> SEQUENCE: 8

Arg Arg Arg Trp Trp Trp
1               5

<210> SEQ ID NO 9
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (6)..(6)
<223> OTHER INFORMATION: AMIDATION

```
<400> SEQUENCE: 9

Lys Phe Lys Phe Lys Phe
1               5

<210> SEQ ID NO 10
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (6)..(6)
<223> OTHER INFORMATION: AMIDATION

<400> SEQUENCE: 10

Lys Tyr Lys Tyr Lys Tyr
1               5

<210> SEQ ID NO 11
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (6)..(6)
<223> OTHER INFORMATION: AMIDATION

<400> SEQUENCE: 11

Phe Lys Phe Lys Phe Lys
1               5

<210> SEQ ID NO 12
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (6)..(6)
<223> OTHER INFORMATION: AMIDATION

<400> SEQUENCE: 12

Phe Lys Phe Lys Pro Val
1               5

<210> SEQ ID NO 13
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (6)..(6)
<223> OTHER INFORMATION: AMIDATION

<400> SEQUENCE: 13

Val Lys Val Lys Pro Val
1               5

<210> SEQ ID NO 14
<211> LENGTH: 6
<212> TYPE: PRT
<213> ORGANISM: Artificial Sequence
```

```
<220> FEATURE:
<223> OTHER INFORMATION: Synthetic
<220> FEATURE:
<221> NAME/KEY: MOD_RES
<222> LOCATION: (6)..(6)
<223> OTHER INFORMATION: AMIDATION

<400> SEQUENCE: 14

Phe Ala Leu Lys Lys Leu
1               5

<210> SEQ ID NO 15
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (6)..(6)
<223> OTHER INFORMATION: AMIDATION

<400> SEQUENCE: 15

Arg Lys Thr Trp Pro Trp
1               5

<210> SEQ ID NO 16
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (6)..(6)
<223> OTHER INFORMATION: AMIDATION

<400> SEQUENCE: 16

Phe Lys Leu Ala Pro Trp
1               5

<210> SEQ ID NO 17
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (6)..(6)
<223> OTHER INFORMATION: AMIDATION

<400> SEQUENCE: 17

Lys Trp Lys Lys Pro Val
1               5

<210> SEQ ID NO 18
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (6)..(6)
<223> OTHER INFORMATION: AMIDATION

<400> SEQUENCE: 18

Phe Arg His Phe Arg Trp
1               5
```

```
<210> SEQ ID NO 19
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (6)..(6)
<223> OTHER INFORMATION: AMIDATION

<400> SEQUENCE: 19

Val Ala Lys Leu Ala Lys
1               5

<210> SEQ ID NO 20
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (6)..(6)
<223> OTHER INFORMATION: AMIDATION

<400> SEQUENCE: 20

Phe Ala Lys Leu Ala Lys
1               5

<210> SEQ ID NO 21
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (6)..(6)
<223> OTHER INFORMATION: AMIDATION

<400> SEQUENCE: 21

Lys Phe Lys Ser Phe Lys
1               5

<210> SEQ ID NO 22
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (6)..(6)
<223> OTHER INFORMATION: AMIDATION

<400> SEQUENCE: 22

Lys Trp Lys Lys Leu Ala
1               5

<210> SEQ ID NO 23
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (6)..(6)
```

```
<223> OTHER INFORMATION: AMIDATION

<400> SEQUENCE: 23

Lys Trp Lys Phe Lys Phe
1               5

<210> SEQ ID NO 24
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (6)..(6)
<223> OTHER INFORMATION: AMIDATION

<400> SEQUENCE: 24

Lys Trp Lys Val Phe Lys
1               5

<210> SEQ ID NO 25
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (6)..(6)
<223> OTHER INFORMATION: AMIDATION

<400> SEQUENCE: 25

Val Ala Lys Lys Trp Lys
1               5

<210> SEQ ID NO 26
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (6)..(6)
<223> OTHER INFORMATION: AMIDATION

<400> SEQUENCE: 26

Phe Ala Lys Leu Ala Lys
1               5

<210> SEQ ID NO 27
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (6)..(6)
<223> OTHER INFORMATION: AMIDATION

<400> SEQUENCE: 27

Lys Leu Ala Lys Leu Leu
1               5

<210> SEQ ID NO 28
<211> LENGTH: 6
<212> TYPE: PRT
```

```
<213> ORGANISM: Artificial Sequence
<220> FEATURE:
<223> OTHER INFORMATION: Synthetic
<220> FEATURE:
<221> NAME/KEY: MOD_RES
<222> LOCATION: (6)..(6)
<223> OTHER INFORMATION: AMIDATION

<400> SEQUENCE: 28

Leu Ala Lys Leu Ala Lys
1               5

<210> SEQ ID NO 29
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (6)..(6)
<223> OTHER INFORMATION: AMIDATION

<400> SEQUENCE: 29

Lys Pro Trp Lys Phe Lys
1               5

<210> SEQ ID NO 30
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (6)..(6)
<223> OTHER INFORMATION: AMIDATION

<400> SEQUENCE: 30

Lys Pro Val Trp Pro Trp
1               5

<210> SEQ ID NO 31
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (6)..(6)
<223> OTHER INFORMATION: AMIDATION

<400> SEQUENCE: 31

Lys Pro Val Lys Phe Lys
1               5

<210> SEQ ID NO 32
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (6)..(6)
<223> OTHER INFORMATION: AMIDATION

<400> SEQUENCE: 32

Lys Phe Val Trp Pro Trp
```

<210> SEQ ID NO 33
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (6)..(6)
<223> OTHER INFORMATION: AMIDATION

<400> SEQUENCE: 33

Leu Leu Lys Trp Pro Trp
1               5

<210> SEQ ID NO 34
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (6)..(6)
<223> OTHER INFORMATION: AMIDATION

<400> SEQUENCE: 34

Phe Pro Trp Lys Phe Lys
1               5

<210> SEQ ID NO 35
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (6)..(6)
<223> OTHER INFORMATION: AMIDATION

<400> SEQUENCE: 35

Lys Pro Val Trp Pro Phe
1               5

<210> SEQ ID NO 36
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (6)..(6)
<223> OTHER INFORMATION: AMIDATION

<400> SEQUENCE: 36

Lys Phe Phe Trp Pro Phe
1               5

<210> SEQ ID NO 37
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MOD_RES

```
<222> LOCATION: (6)..(6)
<223> OTHER INFORMATION: AMIDATION

<400> SEQUENCE: 37

Lys Ala Lys Phe Pro Phe
1               5

<210> SEQ ID NO 38
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (6)..(6)
<223> OTHER INFORMATION: AMIDATION

<400> SEQUENCE: 38

Lys Phe Lys Pro Phe Trp
1               5

<210> SEQ ID NO 39
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa  is 1-Nal-OH, where Nal is naphthylalanine
<220> FEATURE:
<221> NAME/KEY: MOD_RES
<222> LOCATION: (6)..(6)
<223> OTHER INFORMATION: AMIDATION

<400> SEQUENCE: 39

Lys Xaa Lys Trp Pro Trp
1               5

<210> SEQ ID NO 40
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (6)..(6)
<223> OTHER INFORMATION: AMIDATION

<400> SEQUENCE: 40

Lys Phe Lys Leu Pro Trp
1               5

<210> SEQ ID NO 41
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (6)..(6)
<223> OTHER INFORMATION: AMIDATION

<400> SEQUENCE: 41

Lys Phe Lys Trp Pro Trp
1               5
```

```
<210> SEQ ID NO 42
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (6)..(6)
<223> OTHER INFORMATION: AMIDATION

<400> SEQUENCE: 42

Lys Trp Lys Trp Pro Trp
1               5

<210> SEQ ID NO 43
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (6)..(6)
<223> OTHER INFORMATION: AMIDATION

<400> SEQUENCE: 43

Lys Trp Lys Trp Phe Trp
1               5

<210> SEQ ID NO 44
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (6)..(6)
<223> OTHER INFORMATION: AMIDATION

<400> SEQUENCE: 44

Lys Phe Lys Trp Phe Trp
1               5

<210> SEQ ID NO 45
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (6)..(6)
<223> OTHER INFORMATION: AMIDATION

<400> SEQUENCE: 45

Phe Ala Lys Trp Pro Trp
1               5

<210> SEQ ID NO 46
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (6)..(6)
```

```
<223> OTHER INFORMATION: AMIDATION

<400> SEQUENCE: 46

Val Ala Lys Trp Pro Trp
1               5

<210> SEQ ID NO 47
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (6)..(6)
<223> OTHER INFORMATION: AMIDATION

<400> SEQUENCE: 47

Lys Trp Lys Trp Pro Trp
1               5

<210> SEQ ID NO 48
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (6)..(6)
<223> OTHER INFORMATION: AMIDATION

<400> SEQUENCE: 48

Phe Ala Lys Trp Pro Trp
1               5

<210> SEQ ID NO 49
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (6)..(6)
<223> OTHER INFORMATION: AMIDATION

<400> SEQUENCE: 49

Val Ala Lys Trp Pro Trp
1               5

<210> SEQ ID NO 50
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (6)..(6)
<223> OTHER INFORMATION: AMIDATION

<400> SEQUENCE: 50

Lys Trp Lys Phe Pro Phe
1               5

<210> SEQ ID NO 51
<211> LENGTH: 6
<212> TYPE: PRT
```

```
<213> ORGANISM: Artificial Sequence
<220> FEATURE:
<223> OTHER INFORMATION: Synthetic
<220> FEATURE:
<221> NAME/KEY: MOD_RES
<222> LOCATION: (6)..(6)
<223> OTHER INFORMATION: AMIDATION

<400> SEQUENCE: 51

Lys Trp Lys Trp Gly Trp
1               5

<210> SEQ ID NO 52
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (6)..(6)
<223> OTHER INFORMATION: AMIDATION

<400> SEQUENCE: 52

Lys Leu Lys Trp Pro Trp
1               5

<210> SEQ ID NO 53
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (6)..(6)
<223> OTHER INFORMATION: AMIDATION

<400> SEQUENCE: 53

Lys Trp Lys Leu Ala Leu
1               5

<210> SEQ ID NO 54
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa - addition of octanoic acid via an amide
      bond to the peptide
<220> FEATURE:
<221> NAME/KEY: MOD_RES
<222> LOCATION: (6)..(6)
<223> OTHER INFORMATION: AMIDATION

<400> SEQUENCE: 54

Phe Ala Leu Leu Lys Leu
1               5

<210> SEQ ID NO 55
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
```

```
<223> OTHER INFORMATION: Xaa - addition of octanoic acid via an amide
      bond to the peptide
<220> FEATURE:
<221> NAME/KEY: MOD_RES
<222> LOCATION: (6)..(6)
<223> OTHER INFORMATION: AMIDATION

<400> SEQUENCE: 55

Lys Phe Lys Trp Pro Trp
1               5

<210> SEQ ID NO 56
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa - addition of octanoic acid via an amide
      bond to the peptide
<220> FEATURE:
<221> NAME/KEY: MOD_RES
<222> LOCATION: (6)..(6)
<223> OTHER INFORMATION: AMIDATION

<400> SEQUENCE: 56

Lys Trp Lys Trp Phe Trp
1               5

<210> SEQ ID NO 57
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa - addition of octanoic acid via an amide
      bond to the peptide
<220> FEATURE:
<221> NAME/KEY: MOD_RES
<222> LOCATION: (6)..(6)
<223> OTHER INFORMATION: AMIDATION

<400> SEQUENCE: 57

Lys Phe Lys Trp Phe Trp
1               5

<210> SEQ ID NO 58
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa = fluorinated phenylalanine
<220> FEATURE:
<221> NAME/KEY: MOD_RES
<222> LOCATION: (6)..(6)
<223> OTHER INFORMATION: AMIDATION

<400> SEQUENCE: 58

Xaa Ala Leu Leu Lys Leu
1               5

<210> SEQ ID NO 59
```

```
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa = fluorinated phenylalanine
<220> FEATURE:
<221> NAME/KEY: MOD_RES
<222> LOCATION: (6)..(6)
<223> OTHER INFORMATION: AMIDATION

<400> SEQUENCE: 59

Lys Xaa Lys Trp Pro Trp
1               5

<210> SEQ ID NO 60
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: Xaa = fluorinated phenylalanine
<220> FEATURE:
<221> NAME/KEY: MOD_RES
<222> LOCATION: (6)..(6)
<223> OTHER INFORMATION: AMIDATION

<400> SEQUENCE: 60

Lys Trp Lys Trp Xaa Trp
1               5

<210> SEQ ID NO 61
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa = fluorinated phenylalanine
<220> FEATURE:
<221> NAME/KEY: MISC_FEATURE
<222> LOCATION: (5)..(5)
<223> OTHER INFORMATION: Xaa = fluorinated phenylalanine
<220> FEATURE:
<221> NAME/KEY: MOD_RES
<222> LOCATION: (6)..(6)
<223> OTHER INFORMATION: AMIDATION

<400> SEQUENCE: 61

Lys Xaa Lys Trp Xaa Trp
1               5

<210> SEQ ID NO 62
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: Xaa = 1-Nal-OH, where Nal is naphthylalanine
<220> FEATURE:
<221> NAME/KEY: MOD_RES
<222> LOCATION: (6)..(6)
```

<223> OTHER INFORMATION: AMIDATION

<400> SEQUENCE: 62

Lys Trp Lys Trp Xaa Trp
1               5

<210> SEQ ID NO 63
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: Z = 2-Nal-OH, where Nal is naphthylalanine
<220> FEATURE:
<221> NAME/KEY: MOD_RES
<222> LOCATION: (6)..(6)
<223> OTHER INFORMATION: AMIDATION

<400> SEQUENCE: 63

Lys Trp Lys Trp Glx Trp
1               5

<210> SEQ ID NO 64
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (6)..(6)
<223> OTHER INFORMATION: AMIDATION

<400> SEQUENCE: 64

Lys Trp Lys Trp Leu Pro Trp
1               5

<210> SEQ ID NO 65
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (6)..(6)
<223> OTHER INFORMATION: AMIDATION

<400> SEQUENCE: 65

Lys Trp Lys Trp Pro Pro Trp
1               5

<210> SEQ ID NO 66
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (6)..(6)
<223> OTHER INFORMATION: AMIDATION

<400> SEQUENCE: 66

Lys Trp Lys Trp Pro Gly Trp
1               5

```
<210> SEQ ID NO 67
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (6)..(6)
<223> OTHER INFORMATION: AMIDATION

<400> SEQUENCE: 67

Lys Pro Lys Trp Pro Pro Trp
1               5

<210> SEQ ID NO 68
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (6)..(6)
<223> OTHER INFORMATION: AMIDATION

<400> SEQUENCE: 68

Lys Phe Lys Trp Pro Pro Trp
1               5

<210> SEQ ID NO 69
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: addition of heptanoic acid via an amide bond to
      the peptide.
<220> FEATURE:
<221> NAME/KEY: MOD_RES
<222> LOCATION: (6)..(6)
<223> OTHER INFORMATION: AMIDATION

<400> SEQUENCE: 69

Lys Phe Lys Trp Pro Trp
1               5

<210> SEQ ID NO 70
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: addition of heptanoic acid via an amide bond to
      the peptide.
<220> FEATURE:
<221> NAME/KEY: MOD_RES
<222> LOCATION: (6)..(6)
<223> OTHER INFORMATION: AMIDATION

<400> SEQUENCE: 70

Lys Phe Lys Trp Pro Trp
1               5
```

```
<210> SEQ ID NO 71
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: addition of caproic acid via an amide bond to
      the peptide.
<220> FEATURE:
<221> NAME/KEY: MOD_RES
<222> LOCATION: (6)..(6)
<223> OTHER INFORMATION: AMIDATION

<400> SEQUENCE: 71

Lys Phe Lys Trp Pro Trp
1               5

<210> SEQ ID NO 72
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: addition of lauric acid via an amide bond to
      the peptide.
<220> FEATURE:
<221> NAME/KEY: MOD_RES
<222> LOCATION: (6)..(6)
<223> OTHER INFORMATION: AMIDATION

<400> SEQUENCE: 72

Lys Phe Lys Trp Pro Trp
1               5

<210> SEQ ID NO 73
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: addition of palmitic acid via an amide bond to
      the peptide
<220> FEATURE:
<221> NAME/KEY: MOD_RES
<222> LOCATION: (6)..(6)
<223> OTHER INFORMATION: AMIDATION

<400> SEQUENCE: 73

Lys Phe Lys Trp Pro Trp
1               5

<210> SEQ ID NO 74
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Addition of stearic acid via an amide bond to
      the peptide.
<220> FEATURE:
<221> NAME/KEY: MOD_RES
```

```
<222> LOCATION: (6)..(6)
<223> OTHER INFORMATION: AMIDATION

<400> SEQUENCE: 74

Lys Phe Lys Trp Pro Trp
1               5

<210> SEQ ID NO 75
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: addition of oleic acid via an amide bond to the
      peptide.
<220> FEATURE:
<221> NAME/KEY: MOD_RES
<222> LOCATION: (6)..(6)
<223> OTHER INFORMATION: AMIDATION

<400> SEQUENCE: 75

Lys Phe Lys Trp Pro Trp
1               5

<210> SEQ ID NO 76
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: addition of 8-aminocaprylic acid via an amide
      bond to the peptide
<220> FEATURE:
<221> NAME/KEY: MOD_RES
<222> LOCATION: (6)..(6)
<223> OTHER INFORMATION: AMIDATION

<400> SEQUENCE: 76

Lys Phe Lys Trp Pro Trp
1               5

<210> SEQ ID NO 77
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Addition of myristic acid via an amide bond to
      the peptide
<220> FEATURE:
<221> NAME/KEY: MOD_RES
<222> LOCATION: (6)..(6)
<223> OTHER INFORMATION: AMIDATION

<400> SEQUENCE: 77

Lys Phe Lys Trp Pro Trp
1               5

<210> SEQ ID NO 78
<211> LENGTH: 6
<212> TYPE: PRT
<213> ORGANISM: Artificial Sequence
```

```
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: addition of pentadecanoic acid via an amide
      bond to the peptide
<220> FEATURE:
<221> NAME/KEY: MOD_RES
<222> LOCATION: (6)..(6)
<223> OTHER INFORMATION: AMIDATION

<400> SEQUENCE: 78

Lys Phe Lys Trp Pro Trp
1               5

<210> SEQ ID NO 79
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: addition of undecanoic acid via an amide bond
      to the peptide
<220> FEATURE:
<221> NAME/KEY: MOD_RES
<222> LOCATION: (6)..(6)
<223> OTHER INFORMATION: AMIDATION

<400> SEQUENCE: 79

Lys Phe Lys Trp Pro Trp
1               5

<210> SEQ ID NO 80
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: addition of tridecanoic acid viaan amide bond
      to the peptide
<220> FEATURE:
<221> NAME/KEY: MOD_RES
<222> LOCATION: (6)..(6)
<223> OTHER INFORMATION: AMIDATION

<400> SEQUENCE: 80

Lys Phe Lys Trp Pro Trp
1               5

<210> SEQ ID NO 81
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: addition of octanoic acid via an amide bond to
      the peptide
<220> FEATURE:
<221> NAME/KEY: MISC_FEATURE
<222> LOCATION: (1)..(6)
<223> OTHER INFORMATION: D-form residues
<220> FEATURE:
<221> NAME/KEY: MOD_RES
```

```
<222> LOCATION: (6)..(6)
<223> OTHER INFORMATION: AMIDATION

<400> SEQUENCE: 81

Lys Phe Lys Trp Pro Trp
1               5

<210> SEQ ID NO 82
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(6)
<223> OTHER INFORMATION: D-form residues
<220> FEATURE:
<221> NAME/KEY: MOD_RES
<222> LOCATION: (6)..(6)
<223> OTHER INFORMATION: AMIDATION

<400> SEQUENCE: 82

Lys Phe Lys Trp Pro Trp
1               5

<210> SEQ ID NO 83
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: addition of lauric acid via an amide bond to
      the peptide
<220> FEATURE:
<221> NAME/KEY: MISC_FEATURE
<222> LOCATION: (1)..(6)
<223> OTHER INFORMATION: D-form residues
<220> FEATURE:
<221> NAME/KEY: MOD_RES
<222> LOCATION: (6)..(6)
<223> OTHER INFORMATION: AMIDATION

<400> SEQUENCE: 83

Lys Phe Lys Trp Pro Trp
1               5

<210> SEQ ID NO 84
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: addition of actanoic acid via an amide bond to
      the peptide
<220> FEATURE:
<221> NAME/KEY: MISC_FEATURE
<222> LOCATION: (1)..(6)
<223> OTHER INFORMATION: D-form residues
<220> FEATURE:
<221> NAME/KEY: MOD_RES
<222> LOCATION: (6)..(6)
<223> OTHER INFORMATION: AMIDATION

<400> SEQUENCE: 84

Lys Phe Lys Trp Pro Trp
```

-continued

```
<210> SEQ ID NO 85
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Addition of decanoic acid via an amide bond to
      the peptide
<220> FEATURE:
<221> NAME/KEY: MOD_RES
<222> LOCATION: (6)..(6)
<223> OTHER INFORMATION: AMIDATION

<400> SEQUENCE: 85

Lys Phe Lys Trp Pro Trp
1               5
```